US010869911B2

(12) United States Patent
Pulé et al.

(10) Patent No.: US 10,869,911 B2
(45) Date of Patent: Dec. 22, 2020

(54) CHIMERIC PROTEIN

(71) Applicant: UCL BUSINESS PLC, London (GB)

(72) Inventors: Martin Pulé, London (GB); Brian Philip, London (GB)

(73) Assignee: AUTOLUS LIMITED, London (GB)

( * ) Notice: Subject to any disclaimer, the term of this patent is extended or adjusted under 35 U.S.C. 154(b) by 79 days.

(21) Appl. No.: 15/565,914

(22) PCT Filed: Apr. 12, 2016

(86) PCT No.: PCT/GB2016/051019
§ 371 (c)(1),
(2) Date: Oct. 12, 2017

(87) PCT Pub. No.: WO2016/166521
PCT Pub. Date: Oct. 20, 2016

(65) Prior Publication Data
US 2018/0169189 A1    Jun. 21, 2018

(30) Foreign Application Priority Data

Apr. 13, 2015 (GB) .................................. 1506223.5

(51) Int. Cl.
| | | |
|---|---|---|
| *C07K 14/705* | (2006.01) | |
| *C07K 14/71* | (2006.01) | |
| *C07K 19/00* | (2006.01) | |
| *A61K 38/19* | (2006.01) | |
| *C07K 16/28* | (2006.01) | |
| *C07K 14/725* | (2006.01) | |
| *A61P 35/00* | (2006.01) | |
| *A61K 35/17* | (2015.01) | |
| *A61K 39/395* | (2006.01) | |

(52) U.S. Cl.
CPC ............ *A61K 38/191* (2013.01); *A61K 35/17* (2013.01); *A61K 39/39558* (2013.01); *A61P 35/00* (2018.01); *C07K 14/7051* (2013.01); *C07K 16/2887* (2013.01); *C07K 2317/732* (2013.01); *C07K 2317/734* (2013.01); *C07K 2319/00* (2013.01); *C07K 2319/03* (2013.01)

(58) Field of Classification Search
CPC ............ C07K 2319/00; C07K 2319/03; C07K 2317/73
See application file for complete search history.

(56) References Cited

U.S. PATENT DOCUMENTS

2012/0301447 A1* 11/2012 Jensen .................. C07K 14/71
424/93.21

FOREIGN PATENT DOCUMENTS

| WO | WO-01/00854 A2 | 1/2001 |
|---|---|---|
| WO | WO-2008063771 A2 | 5/2008 |
| WO | WO-2014/076292 A1 | 5/2014 |
| WO | WO-2015/152417 A1 | 10/2015 |

OTHER PUBLICATIONS

English Translation of WO 2015/152417, pub. date: Oct. 8, 2015.*
Amara et al., Cell surface tagging and a suicide mechanism in a single chimeric human protein, Hum. Gene Ther., 10(16):2651-5 (1999).
Berinstein et al., Association of serum Rituximab (IDEC-C2B8) concentration and anti-tumor response in the treatment of recurrent low-grade or follicular non-Hodgkin's lymphoma, Ann. Oncol., 9(9):995-1001 (1998).
Di Stasi et al., Inducible apoptosis as a safety switch for adoptive cell therapy, N. Engl. J. Med., 365(18):1673-83 (2011).
International Application No. PCT/GB2016/051019, International Preliminary Report on Patentability, dated Oct. 17, 2017.
International Application No. PCT/GB2016/051019, International Search Report and Written Opinion, dated May 30, 2016.
Introna et al., Genetic modification of human T cells with CD20: a strategy to purify and lyse transduced cells with anti-CD20 antibodies, Hum. Gene Ther., 11(4):611-20 (2000).
Iuliucci et al., Intravenous safety and pharmacokinetics of a novel dimerizer drug, AP1903, in healthy volunteers, J. Clin. Pharmacol., 41(8):870-9 (2001).
Kieback et al., A safeguard eliminates T cell receptor gene-modified autoreactive T cells after adoptive transfer, Proc. Natl. Acad. Sci. USA, 105(2):623-8 (2008).
Marin et al., Comparison of different suicide-gene strategies for the safety improvement of genetically manipulated T cells, Hum. Gene Ther. Methods, 23(6):376-86 (2012).
Philip et al., A highly compact epitope-based marker/suicide gene for easier and safer T-cell therapy, Blood, 124(8):1277-87 (2014).
Tone et al., Death signalobody: inducing conditional cell death in response to a specific antigen, Hum. Gene Ther. Methods, 24(3):141-50 (2013).
Wang et al., A transgene-encoded cell surface polypeptide for selection, in vivo tracking, and ablation of engineered cells, Blood, 118(5):1255-63 (2011).
Wang et al., The Fas-FADD death domain complex structure reveals the basis of DISC assembly and disease mutations, Nat. Structural Mol. Biol., 17:1324-9 (2010).

(Continued)

*Primary Examiner* — Hong Sang
(74) *Attorney, Agent, or Firm* — Marshall, Gerstein & Borun LLP

(57) ABSTRACT

The present invention provides a chimeric protein which comprises a multi-spanning transmembrane protein fused to a FAS endodomain, wherein the multi-spanning transmembrane protein binds an extracellular ligand, leading to activation of the FAS endodomain. The chimeric protein is useful as a suicide gene. The invention also provides a cell, such as a T cell comprising such a chimeric protein, which is useful in adoptive T cell immunotherapy approaches.

21 Claims, 10 Drawing Sheets

Specification includes a Sequence Listing.

(56) References Cited

OTHER PUBLICATIONS

Cang, et al., "Novel CD20 monoclonal antibodies for lymphoma therapy," Journal of Hematology & Oncology, 5;64, 9 pages (2012).
Examination report from Australian Patent Application No. 2016250200 dated Mar. 5, 2020.
First Office action issued in Chinese Application No. 201680021442.1, dated Jul. 2, 2020.

* cited by examiner

CHIMERIC PROTEIN

CROSS-REFERENCE TO RELATED APPLICATIONS

This application is a U.S. national stage of International Application No. PCT/GB2016/051019, filed Apr. 12, 2016, which claims priority benefit of Application No. 1506223.5, filed on Apr. 13, 2015, in the United Kingdom.

INCORPORATION BY REFERENCE OF MATERIALS SUBMITTED ELECTRONICALLY

This application contains, as a separate part of the disclosure, a Sequence Listing in computer readable form (Filename: 52470_Seqlisting.txt; Size: 30,486 bytes; Created: Sept. 25, 2017), which is incorporated by reference in its entirety.

FIELD OF THE INVENTION

The present invention relates to a chimeric protein useful in adoptive cell therapy (ACT). The chimeric protein can act as a suicide gene enabling cells expressing the chimeric protein to be deleted. The present invention also provides a nucleic acid encoding such a chimeric protein, a cell comprising such a nucleic acid and therapeutic uses thereof.

BACKGROUND TO THE INVENTION

Adoptive immunotherapy is an established and evolving therapeutic approach. In the setting of allogeneic haematopoietic stem cell transplantation (HSCT), donor lymphocyte infusions (DLI) are frequently given to treat relapse of haematological malignancies. Tumour infiltrating lymphocytes (TILs) are effective in treating metastatic melanoma. Genetic engineering of T-cells greatly increases the scope and potency of T-cell therapy: T-cell receptor transfer allows targeting of intracellular cancer antigens, while chimeric antigen receptors (CAR) allow targeting of surface cancer or lineage specific antigens. Clinical responses have been observed with both approaches, and numerous further trials are underway.

Acute adverse events can occur following adoptive immunotherapy. Graft-versus-host disease (GvHD) is a common and serious complication of DLI. Administration of engineered T-cells has also resulted in toxicity. For instance, on-target off-tumour toxicity has been reported in native T-cell receptor transfer studies against melanoma antigens; T-cells re-directed to the renal cell carcinoma antigen carbonic anhydrase IX (CAIX) produced unexpected hepatotoxicity. Immune activation syndromes have been reported after CD19 CAR therapy. Finally vector-induced insertional mutagenesis results in a theoretical risk of lymphoproliferative disorders. The incidence and severity of these toxicities is unpredictable. Further, in contrast to a therapeutic protein or small molecules whose adverse events usually abate with the half-life of the therapeutic, T-cells engraft and replicate, potentially resulting in escalating and fulminant toxicity.

Suicide Genes

A suicide-gene is a genetically encoded mechanism which allows selective destruction of adoptively transferred T-cells in the face of unacceptable toxicity. Two suicide-genes have been tested in clinical studies: Herpes Simplex Virus thymidine kinase (HSV-TK) and inducible caspase 9 (iCasp9).

Expression of HSV-TK in T-cells confers susceptibility to ganciclovir. HSV-TK is a highly effective suicide-gene but immunogenicity limits application to clinical settings of profound immunosuppression such as haploidentical HSCT. Further, it precludes the use of Ganciclovir for treatment of cytomegalovirus (CMV) infection.

iCasp9 is activated by an experimental small molecule chemical inducer or dimerizer (CID). This CID is an experimental drug and is considered biologically inert since it does not interact with wild-type FKBP12. However clinical experience with this agent is limited to a very small number of patients (Di Stasi, A. et al. (2011) N. Engl. J. Med. 365, 1673-1683; and Iuliucci, J. D. et al. (2001) J. Clin. Pharmacol. 41, 870-879). It is a relatively large and polar molecule and unlikely to cross the blood-brain barrier. A suicide gene based on CID activation of FAS has been described (Amara et al (1999) Hum. Gene Ther. 10, 2651-2655). This also depends on this CID for activation, and since it does not directly activate the apoptosis cascade, escape (through FAS resistance) is possible.

Mutant human thymidylate kinase (mTMPK) renders cells susceptible to AZT. Recently, HSV-TK, iCasp9 were compared with mTMPK (Marin et al (2012) Hum. Gene Ther. Methods 23, 376-386). mTMPK is not sufficiently active to be useful.

Other suicide genes have been proposed, for instance full-length CD20, which when expressed on a T-cell can render T-cells susceptible to lysis by the therapeutic anti-CD20 antibody Rituximab (Introna, M. et al. (2000) Hum. Gene Ther. 11, 611-620). Other suicide genes have also been described on this theme of antibody recognition: RQR8 renders T-cells susceptible to CD20 but is more compact than the full-length CD20 molecule (Philip, B. et al. (2014) Blood doi:10.1182/blood-2014-01-545020); a truncated version of EGFR (huEGFRt) renders cells susceptible to lysis by anti-EGFR mAbs (Wang, X. et al. (2011) Blood 118, 1255-1263); and a myc epitope tag expressed on a cell surface leaves cells susceptible to lysis with an anti-myc antibody (Kieback et al (2008) Proc. Natl. Acad. Sci. U.S.A 105, 623-628). A major limitation of these antibody dependent approaches is their dependence on bioavailability of a therapeutic antibody at high local concentrations to act. It is known for instance that lytic antibodies are not particularly effective against bulky disease and a limitation of antibody based suicide genes is that cells resident where high antibody concentrations are not reached would escape.

There is thus a need for an alternative suicide gene which is not associated with the disadvantages mentioned above.

Amino and carboxy-termini truncations of CD20 were made, whereby the amino or carboxy terminal endodomains were truncated. These were expressed with eGFP and transfected into 293T cells.

Figure 2:
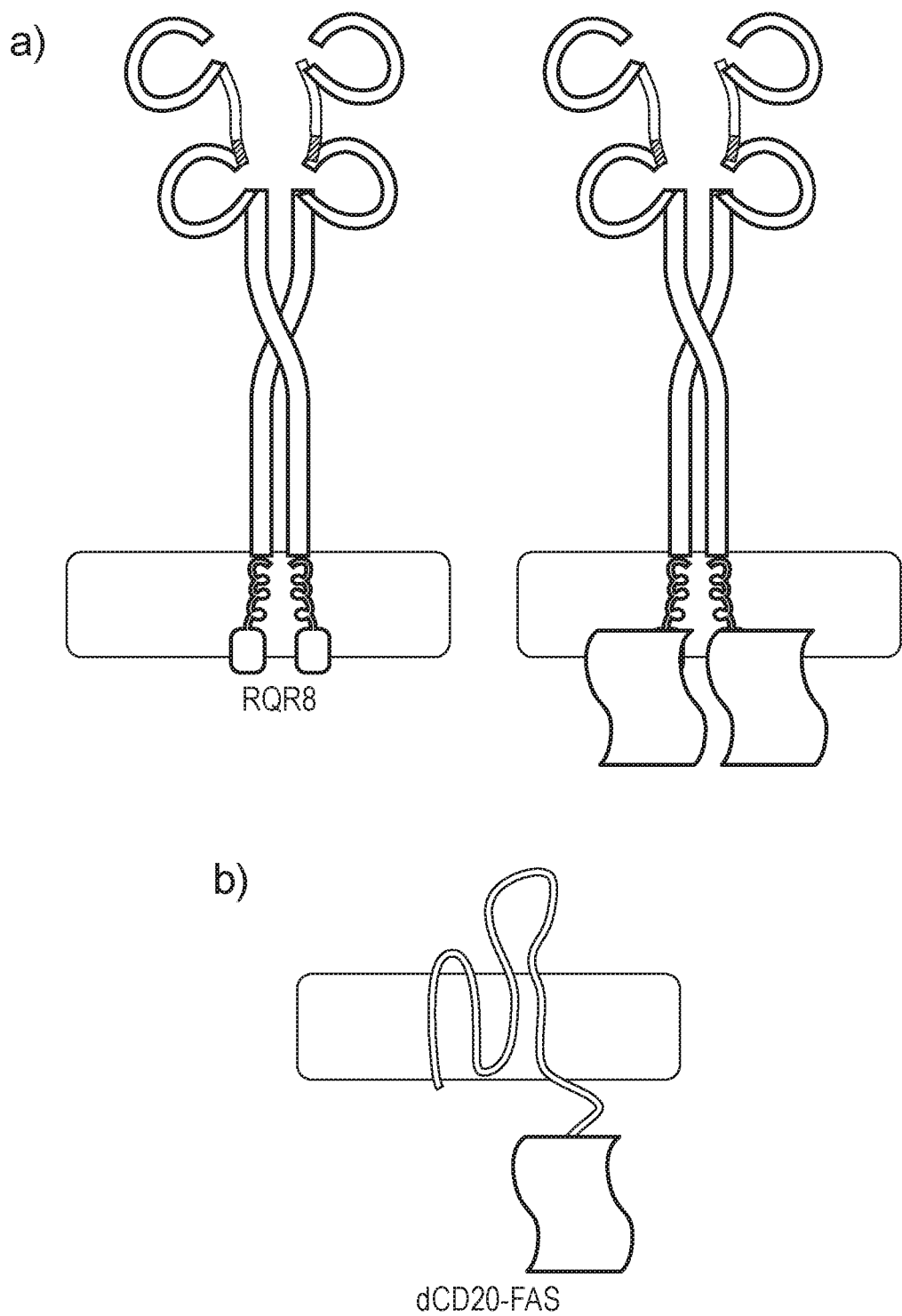

FIG. 2: Cartoon showing a) RQR8 and RQR8-FAS, and b) dCD20-FAS

Figure 3:
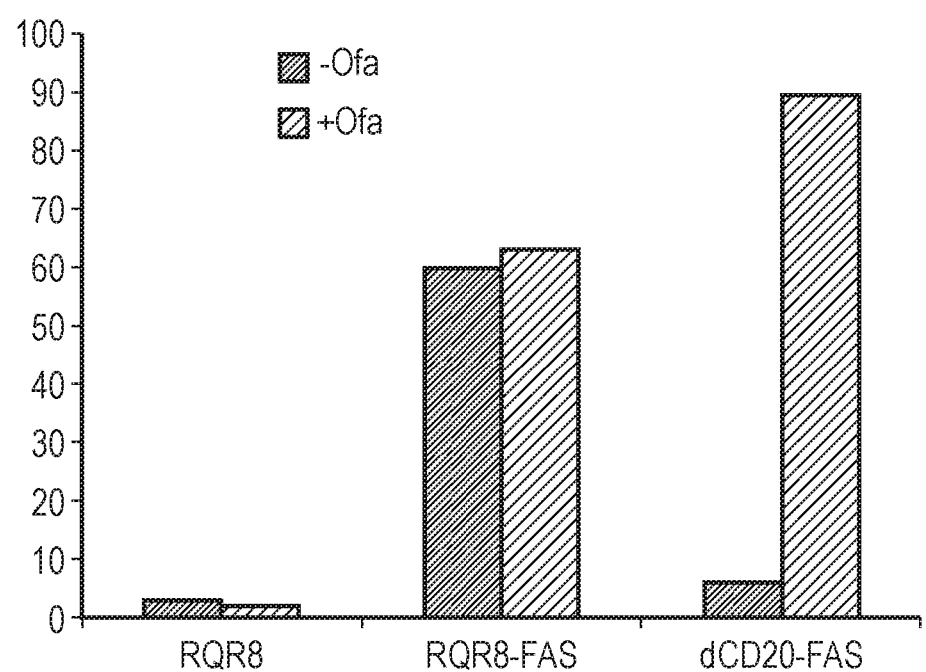

FIG. 3: Comparing the function of RQR8 and RQR8-FAS and dCD20-FAS

Aptoptosis (as a percentage of expressing cells) upon expression and upon activation by Ofatumumab in the different test constructs is shown.

Figure 4:
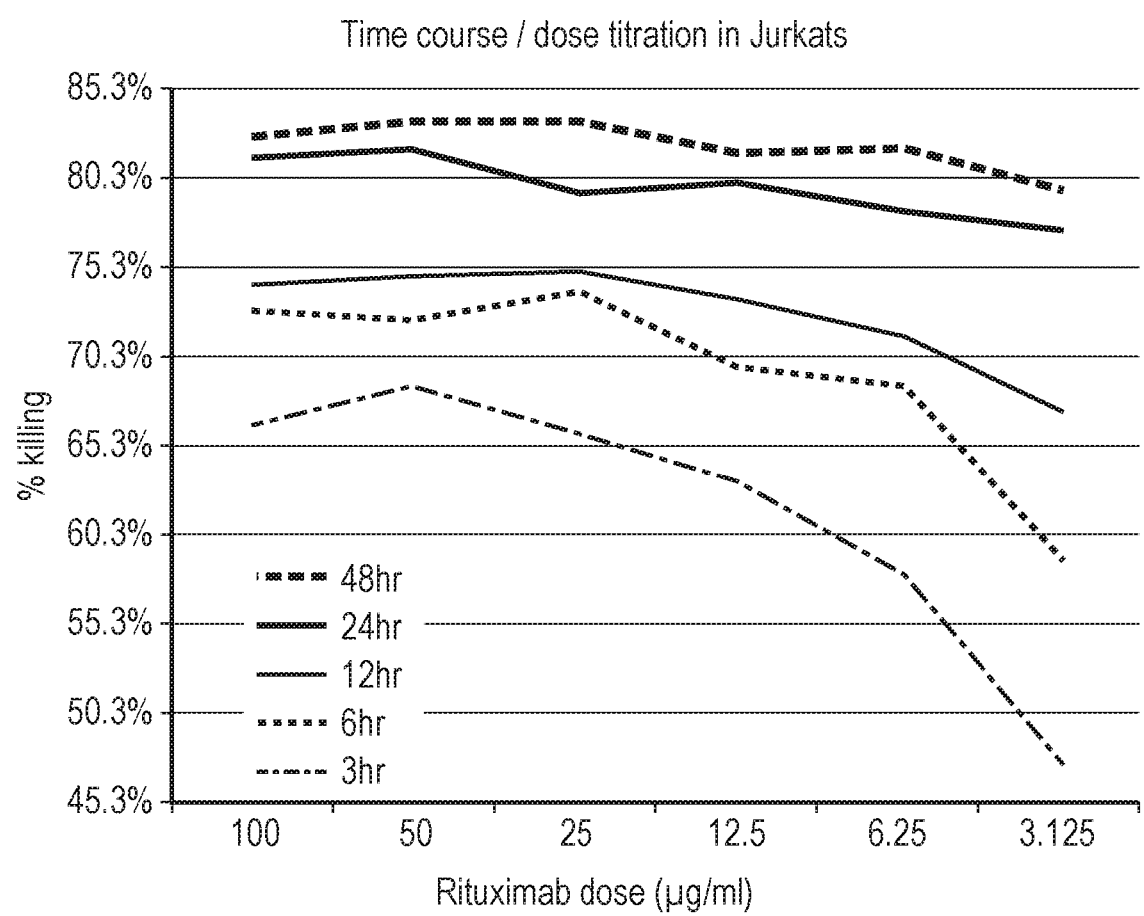

FIG. 4: Sensitivity and time-course of dCD20-FAS to Rituximab

Jurkat T-cells were transduced with dCD20-FAS co-expressed with eGFP. Rituximab induced direct killing is shown over time and at different concentrations of Rituximab.

Figure 5:
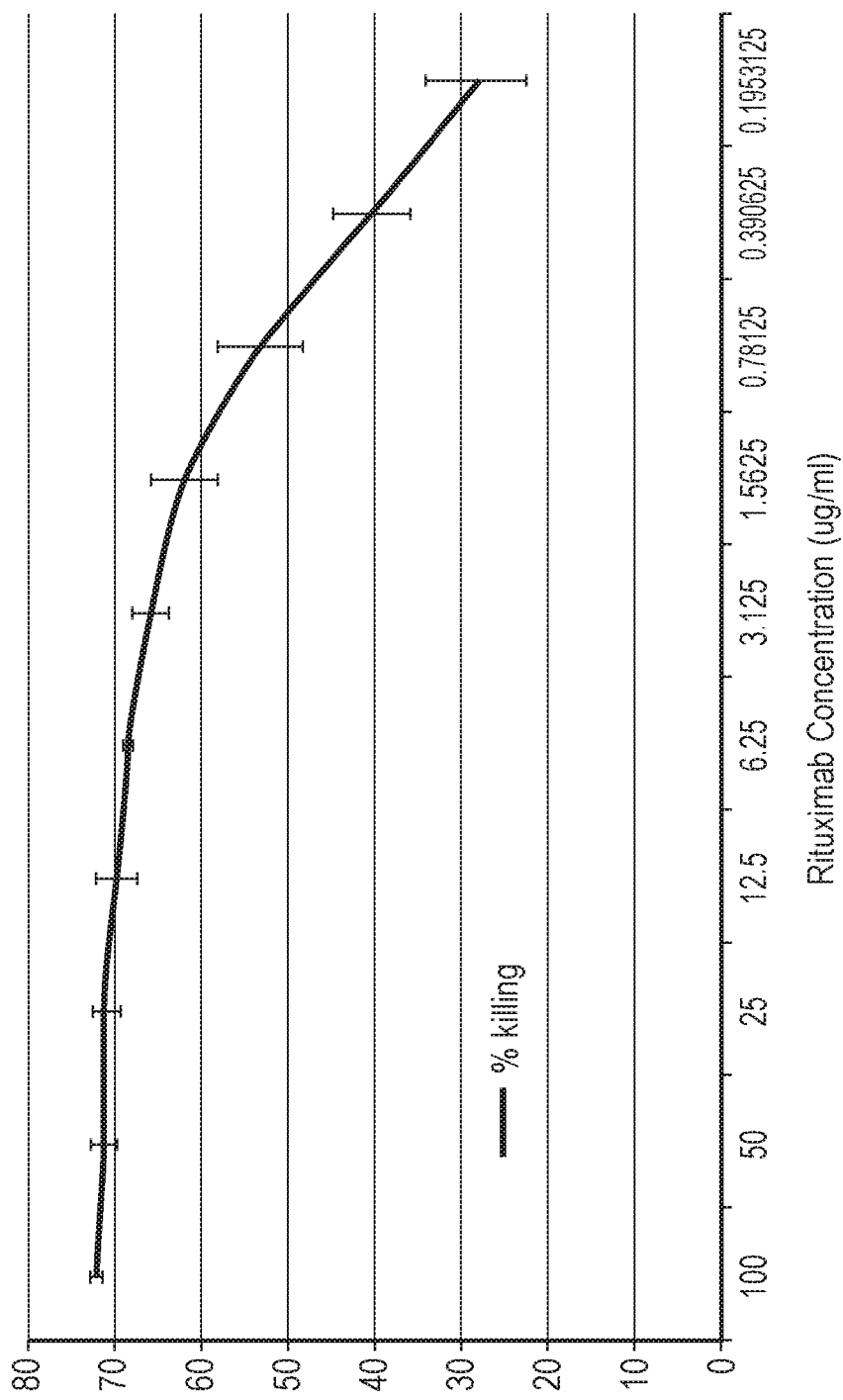

FIG. 5: extended dose-response curve of dCD20-FAS to Rituximab.

Jurkat T-cells transduced with dCD20-FAS and co-expressing eGFP were cultured with increasing dilutions of Rituximab over 48 hours. Direct killing is shown against different concentrations of Rituximab.

Figure 6:
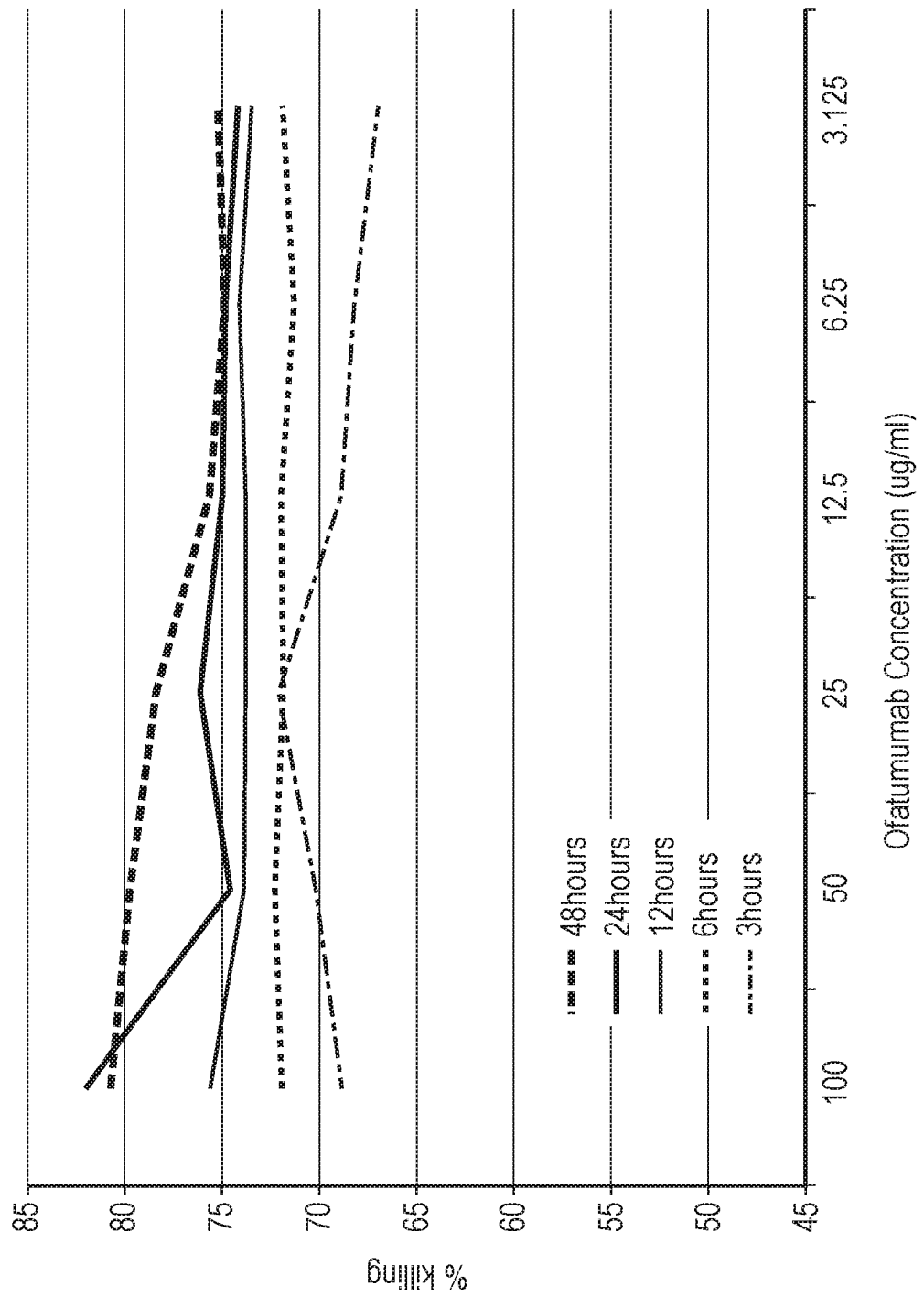

FIG. 6: Sensitivity and time-course of dCD20-FAS to Ofatumumab

Jurkat T-cells were transduced with dCD20-FAS co-expressed with eGFP. Ofatumumab induced direct killing is shown over time and at different concentrations of Ofatumumab.

Figure 7:
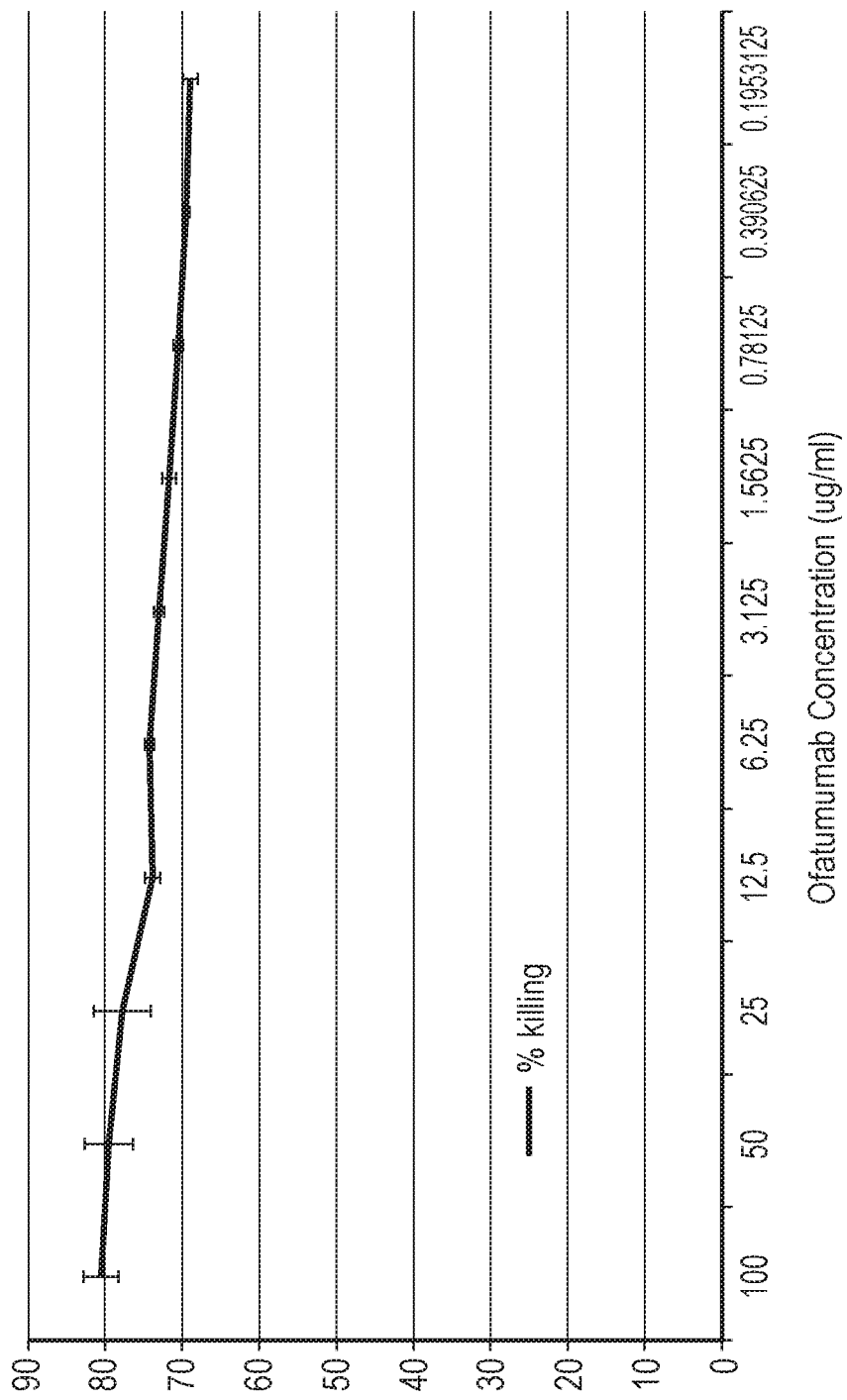

FIG. 7: extended dose-response curve of dCD20-FAS to Ofatumumab.

Jurkat T-cells transduced with dCD20-FAS and co-expressing eGFP were cultured with increasing dilutions of Ofatumumab over 48 hours. Direct killing is shown against different concentrations of Ofatumumab.

Figure 8:
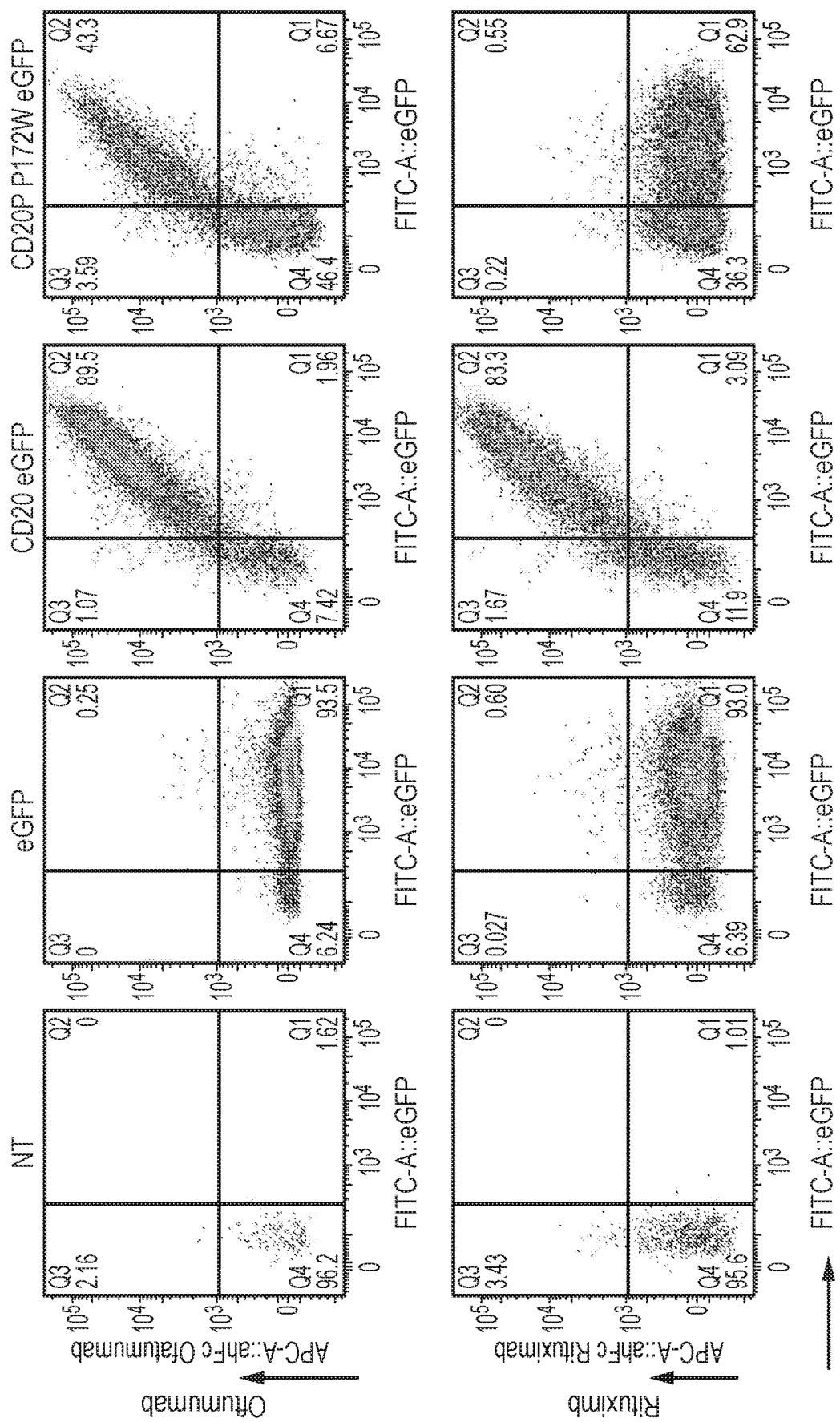

FIG. 8: P172W mutation in CD20 results in Rituximab resistance.

Figure 9:
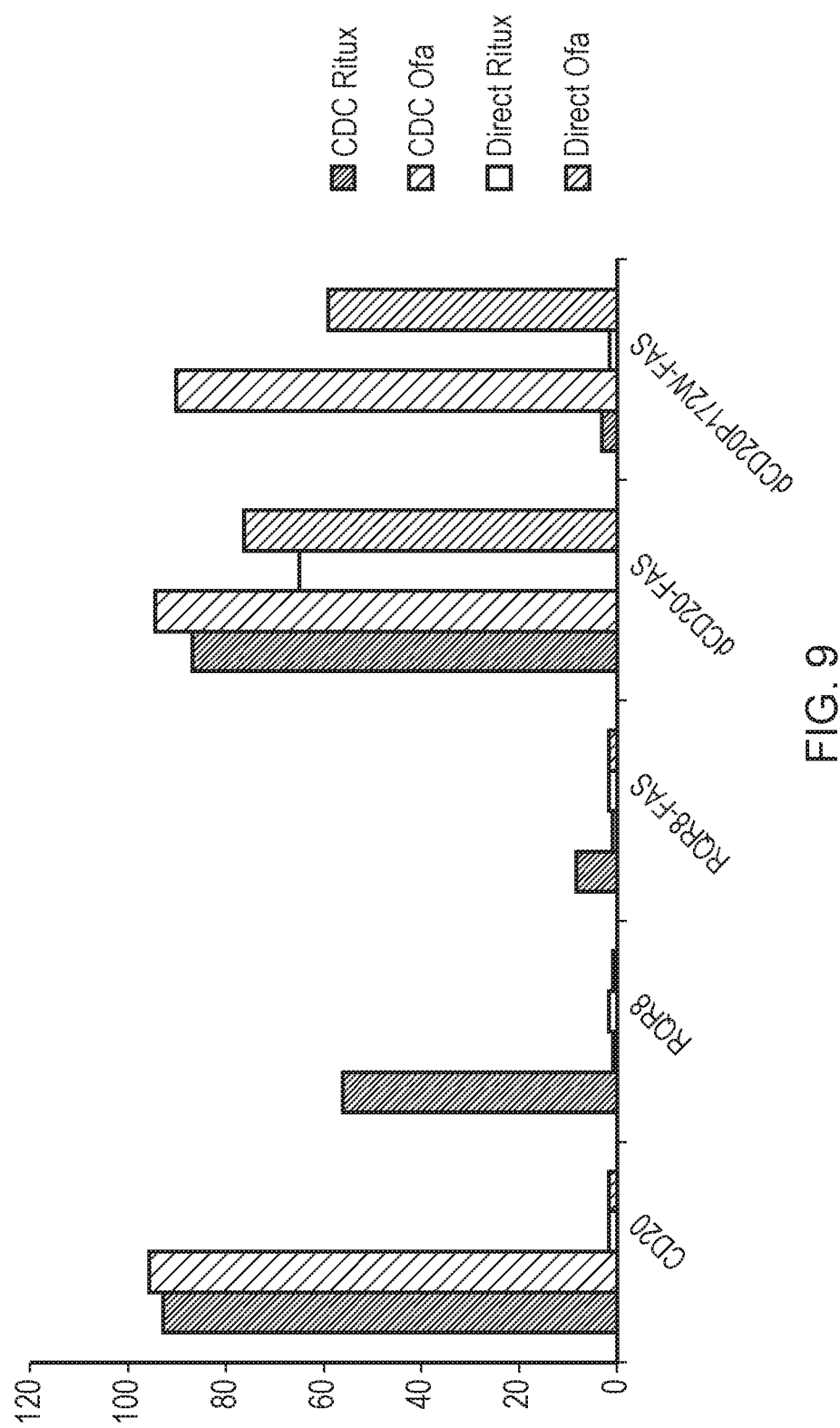

FIG. 9: Direct and CDC mediated killing of primary human T-cells by dCD20-FAS and dCD20$_{P172W}$-FAS.

Figure 10:
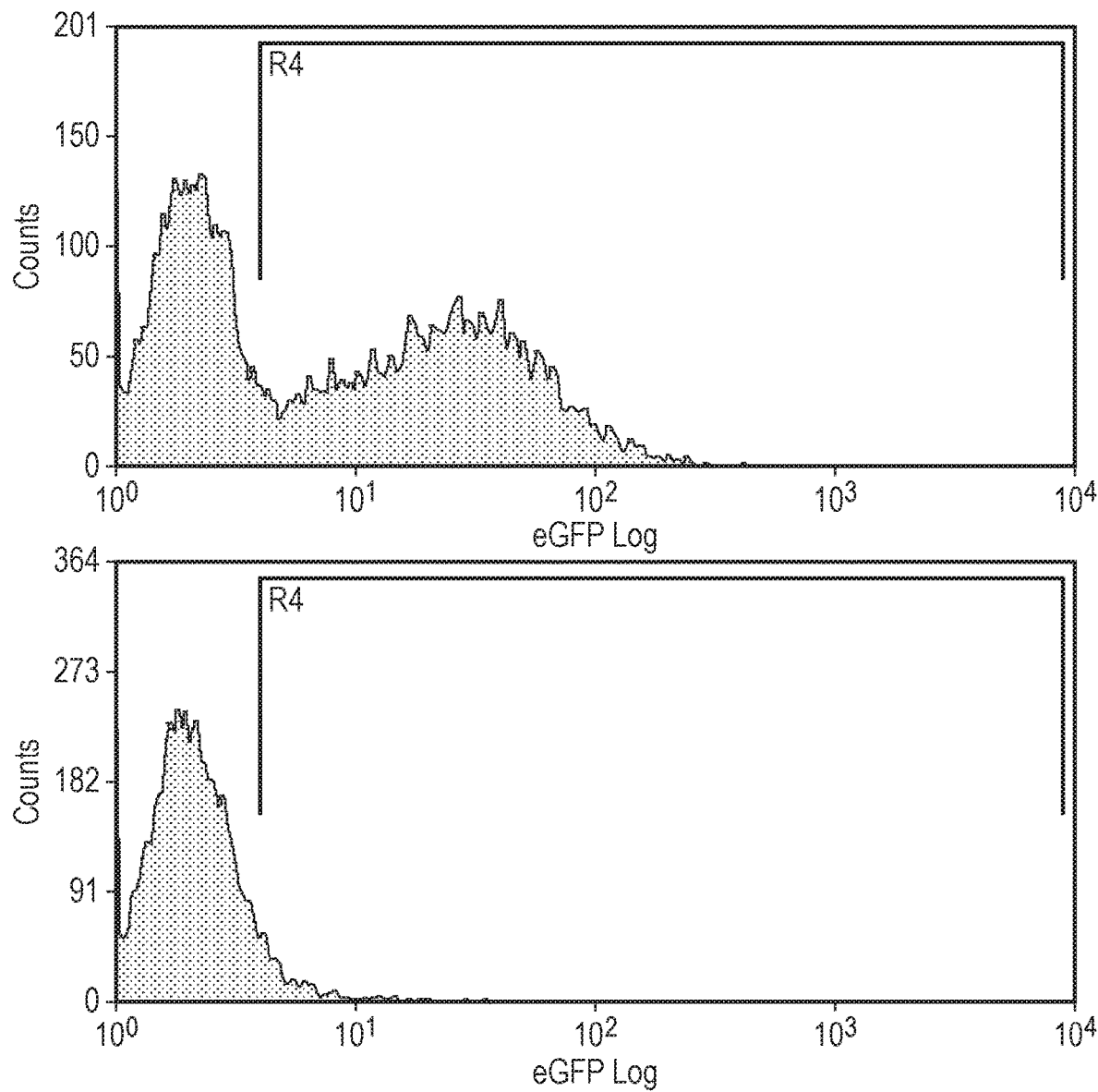

FIG. 10: Example of direct killing by dCD20-FAS of primary T-cells by Ofatumumab.

SUMMARY OF ASPECTS OF THE INVENTION

The present inventors have developed a new suicide gene which is inducible with an extracellular ligand, such as an antibody, and has low basal toxicity and high induced toxicity. The suicide gene is "triple function" in that it can causes suicide by FAS activation, complement-dependent cytotoxicity (CDC) and/or antibody dependent cell-mediated cytotoxicy (ADCC).

Thus, in a first aspect, there is provided a chimeric protein which comprises a multi-spanning transmembrane protein fused to a FAS endodomain, wherein the multi-spanning transmembrane protein binds an extracellular ligand, leading to activation of the FAS endodomain.

The multi-spanning transmembrane protein may be or comprise CD20, or a truncated version thereof lacking the amino-terminal endodomain or the carboxy-terminal endodomain.

The extracellular ligand may be an anti-CD20 monoclonal antibody, such as Rituxumab, Ofatumumab or Veltuzumab. The extracellular ligand may comprise the antigen-binding portion (such as VH/VL or complementarity determining region (CDR) sequences) from an anti-CD20 monoclonal antibody.

The chimeric protein may comprise a FAS endodomain fused to the carboxy-terminus of a truncated version of CD20, lacking the amino-terminal endodomain.

The multi-spanning transmembrane protein may comprise one or more mutations to increase its binding affinity or specificity. Where the multi-spanning transmembrane protein is or comprises CD20 or a part thereof, it may comprise one or more mutations such that it binds Ofatumumab, but not Rituxumab. For example, the CD20 may comprises the mutation P172W, with reference to the full length sequence shown as SEQ ID No. 3.

Where the multi-spanning transmembrane protein is or comprises CD20 or a part thereof, it may comprise the sequence shown as SEQ ID No. 3, 4, 5 or 6.

The multi-spanning transmembrane protein may comprise an endogenous ligand-binding domain, such as CD20, or it may comprise a heterologous ligand binding domain which binds the extracellular ligand.

The FAS endodomain may comprise the sequence shown as SEQ ID No. 20.

In a second aspect, the present invention provides a nucleic acid sequence which encodes a chimeric protein according to the first aspect of the invention.

There is also provided a nucleic acid construct which comprises one or more nucleic acid sequence(s) according to the second aspect of the invention and a nucleic acid sequence encoding a T-cell receptor (TCR) or chimeric antigen receptor (CAR).

In a third aspect, the present invention provides a vector which comprises a nucleic acid sequence according to the second aspect of the invention or a nucleic acid construct as defined above.

The vector may also comprise a nucleotide of interest. The nucleotide of interest may encode a chimeric antigen receptor or a T-cell receptor, such that when the vector is used to transduce a target cell, the target cell co-expresses a chimeric protein according to the first aspect of the invention and a chimeric antigen receptor or T-cell receptor In a fourth aspect, the present invention provides a cell which expresses a chimeric protein according to the first aspect of the invention.

The cell may be, for example, a T-cell, a natural killer (NK) cell or a stem cell.

In a fifth aspect, there is provided a method for making a cell according to the fourth aspect of the invention which comprises the step of transducing or transfecting a cell with a vector according to the third aspect of the invention.

In a sixth aspect there is provided a method for deleting a cell according to the fourth aspect of the invention, which comprises the step of exposing the cells to an extracellular ligand which binds to the multi-spanning transmembrane protein.

In the method of the sixth aspect of the invention, binding of the extracellular ligand may cause one, two or all three of the following:

- activation of the FAS endodomain leading to apoptosis of the cell;
- cross-linking of multi-spanning transmembrane proteins of a plurality of chimeric proteins, leading to complement dependent cytotoxicity (CDC); and
- antibody-dependent cell-mediated cytotoxicity (ADCC)—where the extracellular ligand is an antibody.

The extracellular ligand may be an anti-CD20 monoclonal antibody, such as Rituxumab, Ofatumumab or Veltuzumab.

In a seventh aspect, there is provided a method for preventing or treating a disease in a subject, which comprises the step of administering a cell according to the fourth aspect of the invention to the subject.

The method may comprise the following steps:

(i) transducing or transfecting a sample of cells isolated from a subject with a vector according to the third aspect of the invention, and (ii) administering the transduced/transfected cells to a patient.

The method may be for treating cancer.

In an eighth aspect, the present invention provides a method for preventing and/or treating an pathological immune reaction in a subject caused by administration of a cell according to the fourth aspect of the invention to the subject, which comprises the step of administering an extracellular ligand, capable of binding to the multi-spanning transmembrane protein, to the subject.

The pathological immune reaction may, for example, be: graft-versus-host disease; on-target, off-tumour toxicity; immune activation syndrome; or a lymphoproliferative disorder.

The method for treating a disease in a subject according to the seventh aspect of the invention may comprise the following steps:

(i) administering a cell according to the fourth aspect of the invention to the subject;

(ii) monitoring the subject for the development of a pathological immune reaction; and (iii) administering an extracellular ligand, capable of binding to the multi-spanning transmembrane protein, to the subject if the subject shows signs of developing or having developed a pathological immune reaction.

There is also provided a cell according to the fourth aspect of the invention for use in haematopoietic stem cell transplantation, lymphocyte infusion or adoptive cell transfer.

There is also provided an anti-CD20 antibody for use in preventing or treating a pathological immune reaction caused by administration of a cell according to the fourth aspect of the invention to a subject.

DETAILED DESCRIPTION

Chimeric Protein

The present invention relates to a chimeric protein which acts as a suicide gene. Cells expressing the chimeric protein may be deleted in vivo or in vitro by administration of an extracellular ligand.

The chimeric protein comprises a multi-spanning transmembrane protein fused to a FAS endodomain.

The chimeric protein may comprise the sequence shown as SEQ ID No. 1 or SEQ ID No. 2 or a variant thereof.

```
>dCD20-FAS
                                                                    SEQ ID No. 1
<--------------------------dCD20---------------------------------
MGQSFFMRESKTLGAVQIMNGLFHIALGGLLMIPAGIYAPICVTVWYPLWGGIMYIISGSLLAATEKN

<--------------------------dCD20---------------------------------
SRKCLVKGKMIMNSLSLFAAISGMILSIMDILNIKISHFLKMESLNFIRAHTPYINIYNCEPANPSEK

<--------------------------dCD20---------------------------------
NSPSTQYCYSIQSLFLGILSVMLIFAFFQELVIAGIVENEWKRTCSRPKSNIVLLSAEEKKEQTIEIK

----------------dCD20---------------------------------><-L1-><-------
EEVVGLTETSSQPKNEEDIEIIPIQEEEEEETETNFPEPPQDQESSPIENDSSPSGGGGSEVQKTCRK

-----------------------------dFAS>---------------------------------
HRKENQGSHESPTLNPETVAINLSDVDLSKYITTIAGVMTLSQVKGFVRKNGVNEAKIDEIKNDNVQD

-----------------------------dFAS>-------------------------------->
TAEQKVQLLRNWHQLHGKKEAYDTLIKDLKKANLCTLAEKIQTIILKDITSDSENSNFRNEIQSLV

>dCD20_{P172W}-FAS
                                                                    SEQ ID No. 2
<--------------------------dCD20---------------------------------
MGQSFFMRESKTLGAVQIMNGLFHIALGGLLMIPAGIYAPICVTVWYPLWGGIMYIISGSLLAATEKN

<--------------------------dCD20---------------------------------
SRKCLVKGKMIMNSLSLFAAISGMILSIMDILNIKISHFLKMESLNFIRAHTPYINIYNCEPANWSEK

<--------------------------dCD20---------------------------------
NSPSTQYCYSIQSLFLGILSVMLIFAFFQELVIAGIVENEWKRTCSRPKSNIVLLSAEEKKEQTIEIK

----------------dCD20---------------------------------><-L1-><-------
EEVVGLTETSSQPKNEEDIEIIPIQEEEEEETETNFPEPPQDQESSPIENDSSPSGGGGSEVQKTCRK

-----------------------------dFAS>---------------------------------
HRKENQGSHESPTLNPETVAINLSDVDLSKYITTIAGVMTLSQVKGFVRKNGVNEAKIDEIKNDNVQD

-----------------------------dFAS>-------------------------------->
TAEQKVQLLRNWHQLHGKKEAYDTLIKDLKKANLCTLAEKIQT>IILKDITSDSENSNFRNEIQSLV
```

Variant sequences may have at least 80%, 85%, 90%, 95%, 98% or 99% sequence identity to SEQ ID No. 1 or 2, provided that the sequences provide an effective suicide gene. That is, provided that the sequences retain the capacity to bind to an extracellular ligand, leading to activation of the FAS endodomain.

Multi-Spanning Transmembrane Protein

A transmembrane protein is a protein which spans the entirety of the biological membrane to which it is permanently attached. That is, transmembrane proteins span from one side of a membrane through to the other side of the membrane.

Transmembrane proteins are commonly classified by topology, with reference to the position of the N- and C-terminal domains. Types I, II, and III are single-pass molecules, while type IV relates multiple-pass molecules. The chimeric protein of the present invention comprises a type IV transmembrane protein, which comprises a plurality of membrane-spanning alpha-helices, linked by a series of extracellular and/or intracellular loops.

Type IV transmembrane proteins are subdivided into IV-A, in which the N-terminal domain is targeted to the cytosol; and IV-B, in which the N-terminal domain targeted to the lumen of the endoplasmic reticulum during synthesis. Once the transmembrane protein is expressed at the cell surface, type IV-A transmembrane proteins have an intracellular N-terminal domain, whereas type IV-B transmembrane proteins have an extracellular N-terminal domain.

The chimeric protein may comprise a type IV-A or a type IV-B multi-spanning transmembrane protein. The FAS endodomain may be fused to the N-terminal domain or the C-terminal domain of the transmembrane protein, whichever is located intracellularly.

The multi-spanning transmembrane protein may comprise two or more distinct regions of sequence, such as alpha helices, which span the membrane. The multi-spanning membrane protein may comprise, for example, from 2 to 8, from 3 to 6 or about 4 membrane-spanning portions.

The multi-spanning transmembrane protein may comprise 4 membrane spanning portions and two extracellular loops.

The multi-spanning transmembrane protein comprises a ligand-binding domain which binds to an extracellular ligand. The ligand-binding domain is positioned on the extracellular side of the plasma membrane. The ligand binding domain may be an integral part of the multi-spanning transmembrane protein, such as the Rituximab binding epitope of CD20, or it may be introduced by protein engineering.

The ligand binding domain may be or be inserted in an extracellular loop of the multi-spanning transmembrane protein, i.e. a hydrophilic loop between two hydrophobic, alpha helical, membrane spanning portions. Alternatively the ligand binding domain may be or be inserted in or connected to the end an amino- or carboxyl-terminal extracellular portion of the multi-spanning transmembrane protein, i.e. one of the hydrophilic end portions of the multi-spanning transmembrane protein, provided that is it positioned on the extracellular side of the plasma membrane, rather than the cytosolic side.

Ligand binding domains may be fused to or introduced into a multi-spanning transmembrane protein by recombinant protein engineering.

The extracellular ligand may be a non-naturally occurring ligand, such as an antibody which has been raised against the ligand binding domain of the multi-spanning transmembrane protein.

The ligand-binding domain of the multi-spanning transmembrane protein is capable of binding the extracellular ligand which binding causes activation of the FAS endodomain.

In order to avoid uncontrolled deletion of cells expressing the suicide gene, the multi-spanning protein may not have an endogenous ligand, or may be modified such that it no longer has the capacity to bind any natural ligand(s).

CD20

CD20 is a multi-spanning membrane protein. CD20 is expressed on all stages of B cell development except the first and last: it is present from late pro-B cells through memory cells, but not on either early pro-B cells or plasma blasts and plasma cells. It is expressed on almost all B-cell lymphomas, hairy cell leukemia and B-cell chronic lymphocytic leukemia. CD20 has two extracellular loops: a minor loop and a major loop constrained by a di-sulfide bond. It has an amino-terminal and carboxy-terminal endodomain. CD20 aggregates in lipid rafts when exposed with certain anti-CD20 monoclonal antibodies. The aggregation is dependent on the carboxy terminal endodomain.

The sequence of full-length human CD20 is shown as SEQ ID No. 3.

```
                                              SEQ ID No. 3
MTTPRNSVNGTFPAEPMKGPIAMQSGPKPLFRRMSSLVGPTQSFFMRESK

TLGAVQIMNGLFHIALGGLLMIPAGIYAPICVTVWYPLWGGIMYIISGSL

LAATEKNSRKCLVKGKMIMNSLSLFAAISGMILSIMDILNIKISHFLKME

SLNFIRAHTPYINIYNCEPANPSEKNSPSTQYCYSIQSLFLGILSVMLIF

AFFQELVIAGIVENEWKRTCSRPKSNIVLLSAEEKKEQTIEIKEEVVGLT

ETSSQPKNEEDIEIIPIQEEEEEETETNFPEPPQDQESSPIENDSSP
```

The positions of A170 and P172 are shown in bold and underlined.

The present inventors have shown that it is possible to truncate CD20, at either the amino- or carboxy-terminus, and retain the capacity to be expressed at the cell surface, and the capacity to be recognised by anti-CD20 antibodies such as Rituximab or Ofatumumab.

The multi-spanning transmembrane protein may comprise truncated version of CD20, lacking the amino terminal endodomain. The truncated CD20 may lack up to and including 41 amino acids from the amino terminus. For example, the truncated CD20 may lack between 1 and 41, 5 and 35, or 10-20 amino acids from the amino terminus The truncated CD20 may comprise the sequence shown as SEQ ID No. 4, or a variant thereof.

```
(dCD20)
                                              SEQ ID No. 4
QSFFMRESKTLGAVQIMNGLFHIALGGLLMIPAGIYAPICVTVWYPLWGG

IMYIISGSLLAATEKNSRKCLVKGKMIMNSLSLFAAISGMILSIMDILNI

KISHFLKMESLNFIRAHTPYINIYNCEPANPSEKNSPSTQYCYSIQSLFL

GILSVMLIFAFFQELVIAGIVENEWKRTCSRPKSNIVLLSAEEKKEQTIE

IKEEVVGLTETSSQPKNEEDIEIIPIQEEEEEETETNFPEPPQDQESSPI

ENDSSP
```

The multi-spanning transmembrane protein may comprise truncated version of CD20, lacking the carboxy terminal endodomain. The truncated CD20 may lack up to and including 61 amino acids from the carboxy terminus. For example, the truncated CD20 may lack between 1 and 61, 5 and 55, or 10-20 amino acids from the carboxy terminus The truncated CD20 may comprise the sequence shown as SEQ ID No. 5, or a variant thereof.

```
(CD20d)
                                              SEQ ID No. 5
MGTTPRNSVNGTFPAEPMKGPIAMQSGPKPLFRRMSSLVGPTQSFFMRES

KTLGAVQIMNGLFHIALGGLLMIPAGIYAPICVTVWYPLWGGIMYIISGS

LLAATEKNSRKCLVKGKMIMNSLSLFAAISGMILSIMDILNIKISHFLKM

ESLNFIRAHTPYINIYNCEPANPSEKNSPSTQYCYSIQSLFLGILSVMLI

FAFFQELVIAGIVENEWKRTCSRPKSNIVLLSAEEKK
```

The CD20 may be engineered to increase binding affinity or increase selectivity of binding to the extracellular ligand. For example, CD20 may comprise a mutation at position A170 and/or P172 with reference to the numbering of the full-length CD20 sequence shown as SEQ ID No. 3 above (shown in bold and underlined in SEQ ID No. 3). The mutation may, for example be an addition, deletion or substitution.

In particular, the CD20 sequence may comprise the mutation P172W, such that the variant CD20 binds Ofatumumab, but not Rituximab.

The chimeric protein may comprise a truncated version of CD20, lacking the amino terminal endodomain, which comprises the mutation P172W with reference to the position numbering of full-length CD20, as shown in SEQ ID No. 3. This sequence is shown as SEQ ID No. 6 below.

```
(dCD20_{P172W})
                                          SEQ ID No. 6
QSFFMRESKTLGAVQIMNGLFHIALGGLLMIPAGIYAPICVTVWYPLWGG

IMYIISGSLLAATEKNSRKCLVKGKMIMNSLSLFAAISGMILSIMDILNI

KISHFLKMESLNFIRAHTPYINIYNCEPANWSEKNSPSTQYCYSIQSLFL

GILSVMLIFAFFQELVIAGIVENEWKRTCSRPKSNIVLLSAEEKKEQTIE

IKEEVVGLTETSSQPKNEEDIEIIPIQEEEEEETETNFPEPPQDQESSPI

ENDSSP
```

The ligand-binding domain may bind an anti-CD20 mAb such as Rituximab.

The ligand binding domain may comprise the Rituximab-binding epitope sequence from CD20, which has the sequence shown as SEQ ID No. 7.

```
                                          (SEQ ID No. 7)
CEPANPSEKNSPSTQYC
```

Perosa et al (2007, J. Immunol 179:7967-7974) describe a series of cysteine-constrained 7-mer cyclic peptides, which bear the antigenic motif recognised by the anti-CD20 mAb Rituximab but have different motif-surrounding amino acids. Eleven peptides were described in all, as shown in the following table:

| Peptide | Insert sequence |
|---|---|
| R15-C | acPYANPSLc (SEQ ID No. 8) |
| R3-C | acPYSNPSLc (SEQ ID No. 9) |
| R7-C | acPFANPSTc (SEQ ID No. 10) |
| R8-, R12-, R18-C | acNFSNPSLc (SEQ ID No. 11) |
| R14-C | acPFSNPSMc (SEQ ID No. 12) |
| R16-C | acSWANPSQc (SEQ ID No. 13) |
| R17-C | acMFSNPSLc (SEQ ID No. 14) |
| R19-C | acPFANPSMc (SEQ ID No. 15) |
| R2-C | acWASNPSLc (SEQ ID No. 16) |
| R10-C | acEHSNPSLc (SEQ ID No. 17) |
| R13-C | acWAANPSMc (SEQ ID No. 18) |

Li et al (2006 Cell Immunol 239:136-43) also describe mimetopes of Rituximab, including the sequence:

```
                                          (SEQ ID No. 19)
QDKLTQWPKWLE.
```

The chimeric protein of the present invention may comprises a Rituximab-binding epitope having the an amino acid sequence as shown in any of SEQ ID No. 7 to 19 or a variant thereof which retains Rituximab-binding activity.

A variant Rituximab-binding epitope is based on the sequence amino acid sequence as shown in any of SEQ ID No. 7 to 19 but comprises one or more amino acid mutations, such as amino acid insertions, substitutions or deletions, provided that the epitope retains Rituximab-binding activity. The sequence may comprise 3 or fewer, 2 or fewer, or one amino acid mutation.

A Rituximab binding epitope such as one having the an amino acid sequence as shown in any of SEQ ID No. 7 to 19 or a variant thereof may be introduced into an extracellular loop or an extracellular amino or carboxy-terminal sequence of a multi-spanning transmembrane protein by methods know in the art, such as using recombinant techniques.

Fas Endodomain

The FAS receptor (FasR), also known as apoptosis antigen 1 (APO-1 or APT), cluster of differentiation 95 (CD95) or tumour necrosis factor receptor superfamily member 6 (TNFRSF6) is a death receptor on the surface of cells that leads to programmed cell death (apoptosis).

The mature FAS protein has 319 amino acids, has a predicted molecular weight of 48 kD and is divided into 3 domains: an extracellular domain, a transmembrane domain, and a cytoplasmic domain. The extracellular domain has 157 amino acids and is rich in cysteine residues. The transmembrane and cytoplasmic domains have 17 and 145 amino acids respectively.

The cytoplasmic or endodomain of FAS contains the "Death Domain".

The physiological ligand for FAS is FASL which is a member of the TNF cytokine family. FASL is expressed on activated T cells, natural killer (NK) cells and other cells of the immune system. When FAS binds to its ligand, a caspase cascade is initiated within the cell that eventually leads to its death.

FAS forms the death-inducing signalling complex (DISC) upon ligand binding. Membrane-anchored FAS ligand trimer on the surface of an adjacent cell causes oligomerization of FAS. Upon ensuing death domain (DD) aggregation, the receptor complex is internalized via the cellular endosomal machinery. This allows the adaptor molecule FADD to bind the death domain of FAS through its own death domain.

FAS plays critical roles in the immune system, including the killing of pathogen-infected cells and the death of obsolete and autoreactive lymphocytes. In this way, in the immune system, FAS protects against autoimmunity and lymphoid tumor development. FAS triggers apoptosis through FADD-mediated recruitment and activation of caspase-8. While in non-lymphoid tissue e.g. hepatocytes, FAS-induced apoptosis requires amplification through proteolytic activation of the proapoptotic BCL-2 family member BID. Lymphoid cells however are extremely sensitive to FAS activation.

Binding of the extracellular ligand to the multi-spanning transmembrane protein causes activation of the FAS endodomain in a manner analogous to FASL binding FAS. Binding of the extracellular ligand to the multi-spanning transmembrane protein causes aggregation of FAS endodomains, binding of FADD, and activation of caspase-8.

FAS is a key component in a pathway through which auto-reactive lymphocytes are deleted. The chimeric protein of the present invention exploits this pathway as a suicide gene, one of the key applications for which is to stop engineered T-cell responses which are autoreactive (e.g. on-target off-tumour toxicity).

The chimeric protein of the present invention may comprise the cytoplasmic domain of FAS, which corresponds to residues 174-317 of FAS and has the sequence shown as SEQ ID No. 20, or a variant thereof.

```
                                              SEQ ID No. 20
EVQKTCRKHRKENQGSHESPTLNPETVAINLSDVDLSKYITTIAGVMTLS
QVKGFVRKNGVNEAKIDEIKNDNVQDTAEQKVQLLRNWHQLHGKKEAYDT
LIKDLKKANLCTLAEKIQTIILKDITSDSENSNFRNEIQSLV
```

The chimeric protein of the present invention may comprise the "death domain" of FAS, which corresponds to residues 230-314 of the endodomain of FAS and has the sequence shown as SEQ ID No. 29, or a variant thereof.

```
                                              SEQ ID No. 29
SKYITTIAGVMTLSQVKGFVRKNGVNEAKIDEIKNDNVQDTAEQKVQLLR
NWHQLHGKKEAYDTLIKDLKKANLCTLAEKIQTII
```

Variant sequences may have at least 80%, 85%, 90%, 95%, 98% or 99% sequence identity to SEQ ID No. 20 or 29, provided that the FAS variant retains the capacity to trigger apoptosis. That is, provided that the FAS variant retains the capacity to cause DISC assembly upon ligand binding, leading to subsequent caspase-8 activation.

Extracellular Ligand

The extracellular ligand may be any protein or other entity which is capable of binding the ligand-binding domain of the multi-spanning transmembrane portion of the chimeric protein leading to activation of the FAS endodomain.

The term "extracellular" indicates that the ligand is present outside the cell which comprises the chimeric protein of the invention in its cell membrane.

The extracellular ligand may cause clustering of the chimeric protein of the first aspect of the invention in the cell membrane. The extracellular ligand may, itself be lytic (such as rituximab), providing another mechanism whereby cells expressing the chimeric protein are destroyed.

The extracellular ligand may be a soluble ligand (i.e. not membrane-bound).

In order to avoid uncontrolled deletion of cells expressing the suicide gene, the extracellular ligand should not be an endogenous ligand or have any endogenous counterpart which is also capable of binding to the multi-membrane spanning portion of the chimeric protein.

The extracellular ligand may be a synthetic ligand or a natural ligand which is not endogenous to the subject (e.g. derived from a plant or another animal species).

In particular, the extracellular ligand may be an antibody, which term includes antibody fragments and mimetics.

As used herein, "antibody" means a polypeptide having an antigen binding site which comprises at least one complementarity determining region CDR. The antibody may comprise 3 CDRs and have an antigen binding site which is equivalent to that of a domain antibody (dAb). The antibody may comprise 6 CDRs and have an antigen binding site which is equivalent to that of a classical antibody molecule.

The remainder of the polypeptide may be any sequence which provides a suitable scaffold for the antigen binding site and displays it in an appropriate manner for it to bind the antigen. The antibody may be a whole immunoglobulin molecule or a part thereof such as a Fab, F(ab)'2, Fv, single chain Fv (ScFv) fragment or Nanobody. The antibody may be a bifunctional antibody. The antibody may be non-human, chimeric, humanised or fully human.

The antibody may therefore be any functional fragment which retains the antigen specificity of the full antibody.

The extracellular ligand binding domain may, on the other hand, comprise a binding moiety which is not derived from or based on an immunoglobulin. A number of "antibody mimetic" designed repeat proteins (DRPs) have been developed to exploit the binding abilities of non-antibody polypeptides.

Repeat proteins such as ankyrin or leucine-rich repeat proteins are ubiquitous binding molecules which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. DARPins (Designed Ankyrin Repeat Proteins) are one example of an antibody mimetic based on this technology.

For Anticalins, the binding specificity is derived from lipocalins, a family of proteins which perform a range of functions in vivo associated with physiological transport and storage of chemically sensitive or insoluble compounds. Lipocalins have a robust intrinsic structure comprising a highly conserved β-barrel which supports four loops at one terminus of the protein. These loops for the entrance to a binding pocket and conformational differences in this part of the molecule account for the variation in binding specificity between different lipocalins.

Avimers are evolved from a large family of human extracellular receptor domains by in vitro exon shuffling and phage display, generating multi-domain proteins with binding and inhibitory properties.

Versabodies are small proteins of 3-5 kDa with >15% cysteines which form a high disulfide density scaffold, replacing the hydrophobic core present in most proteins. The replacement of a large number of hydrophobic amino acids, comprising the hydrophobic core, with a small number of disulphides results in a protein that is smaller, more hydrophilic, more resistant to proteases and heat and has a lower density of T-cell epitopes. All four of these properties result in a protein having considerably reduced immunogenicity. They may also be manufactured in *E. coli*, and are highly soluble and stable.

CD20 Monoclonal Antibodies

CD20 is the target of the monoclonal antibodies (mAb) such as rituximab, ofatumumab, veltuzumab, obinutuzumab, ibritumomab, tiuxetan, and tositumomab.

The extracellular ligand may be or comprise on or these CD20 mAb or the binding domain thereof.

Several anti-CD20 antibodies have been approved for therapeutic use or are currently in clinical trial, for example:
  Rituximab for the treatment of non-Hodgkin lymphoma and chronic lymphocytic leukemia (CLL)
  Ofatumumab was approved by FDA in October 2009 for CLL;
  Obinutuzumab was approved by FDA in November 2013 for CLL;

The chimeric mAb rituximab (Rituxan) was the first FDA-approved CD20 monoclonal antibody. It is currently approved to treat CD20 positive B cell malignancies; e.g. non-Hodgkin lymphoma and chronic lymphocytic leukemia (CLL). In addition, it is also approved for use in some autoimmune diseases, including rheumatoid arthritis. Rituximab is being increasingly used in several other autoimmune diseases, such as systemic lupus erythematosus (SLE) or multiple sclerosis. In oncology indications, rituximab was typically used in combination with chemotherapy e.g. the regimen CHOP with Rituximab (R-CHOP) is standard of care for diffuse large B-cell lymphoma. Rituximab is being increasingly used in indolent lymphoproliferative disorders as a monotherapy in a prolonged maintenance phase. Rituximab by far is the most commonly used therapeutic antibody. Consequently a very clear picture of its pharmacological properties has emerged: Rituximab is a highly potent lymphodepleting antibody. It is typically very well tolerated. Although Rituximab monotherapy results in B-cell depletion, increased risks of infection, particularly with short regimens is slight.

Rituximab is a so-called Type I CD20 mAb. Rituximab induces the reorganization of CD20 molecules into lipid rafts and consequently efficiently activate the classical pathway of the complement system. In contrast, type II CD20 mAbs do not have this effect and poorly activate complement. Both types are capable of inducing antibody dependent cell-mediated cytotoxicy (ADCC) in the presence of effector cells.

Rituximab is a genetically engineered chimeric murine/human monoclonal antibody. The antibody is an IgG1 kappa immunoglobulin containing murine light- and heavy-chain variable region sequences and human constant region sequences.

The heavy and light chain variable regions of rituximab as shown as SEQ ID Nos. 21 and 22.

The heavy and light chain variable regions of ofatumumab as shown as SEQ ID Nos. 23 and 24, with the CDR sequences underlined

```
Rituximab heavy chain variable chain sequence
                                      (SEQ ID No. 21)
QVQLQQPGAELVKPGASVKMSCKASGYTFTSYNMHWVKQTPGRGLEWIGA
IYPGNGDTSYNQKFKGKATLTADKSSSTAYMQLSSLTSEDSAVYYCARST
YYGGDWYFNVWGAGTTVTVS
Rituximab light chain variable chain sequence
                                      (SEQ ID No. 22)
QIVLSQSPAILSASPGEKVTMTCRASSSVSYIHWFQQKPGSSPKPWIYAT
SNLASGVPVRFSGSGSGTSYSLTISRVEAEDAATYYCQQWTSNPPTFGGG
TKLEIKR
```

The extracellular ligand which binds the chimeric protein of the invention may be or comprise Rituximab or the binding portions thereof. For example, the extracellular ligand may comprise the heavy chain variable region of rituximab shown as SEQ ID No. 21 and/or the light chain variable region of rituximab shown as SEQ ID No. 22. The extracellular ligand may comprise CDR3 from the heavy chain variable region of rituximab shown as SEQ ID No. 21 and/or CDR3 from the light chain variable region of rituximab shown as SEQ ID No. 22. The extracellular ligand may comprise CDR1, CDR2 and CDR3 from the heavy chain variable region of rituximab shown as SEQ ID No. 21 and/or CDR1, CDR2 and CDR3 from the light chain variable region of rituximab shown as SEQ ID No. 22.

While Rituximab is the first and standard anti-CD20 mAb in clinical use, others have been developed and are in use. The fully human CD20 mAb ofatumumab was approved by the FDA in 2009 for the treatment of CLL patients resistant for both alemtuzumab and fludarabine. Ofatumumab recognition of CD20 differs from that of Rituximab in that it recognizes an overlapping epitope on the small and big extracellular loop of CD20. Ofatumuamb is a type I antibody and is considered to result in even better complement activation than Rituxumab perhaps due to better lipid raft formation. Veltuzumab is a humanized CD20 mAb that carry similar CDR sequences to Rituximab (and hence binds the same epitope). Obinutuzumab (also known as GA101) is an unusual anti-CD20 therapeutic mAb since it is a type II CD20 mAb. Obinutuzumab is under clinical development.

```
Ofatumumab heavy chain variable chain sequence
                                      (SEQ ID No. 23)
EVQLVESGGGLVQPGRSLRLSCAASGFTFNDYAMHWVRQAPGKGLEWVST
ISWNSGSIGYADSVKGRFTISRDNAKKSLYLQMNSLRAEDTALYYCAKDI
QYGNYYYGMDVWGQGTTVTVSS Ofatumumab light chain variable chain sequence
                                      (SEQ ID No. 24)
EIVLTQSPATLSLSPGERATLSCRASQSVSSYLAWYQQKPGQAPRLLIYD
ASNRATGIPARFSGSGSGTDFTLTISSLEPEDFAVYYCQQRSNWPITFGQ
GTRLEIK
```

In the sequences above, the CDr sequences are underlined.

The extracellular ligand which binds the chimeric protein of the invention may be or comprise ofatumumab or the binding portions thereof. For example, the extracellular ligand may comprise the heavy chain variable region of ofatumumab shown as SEQ ID No. 23 and/or the light chain variable region of ofatumumab shown as SEQ ID No. 24. The extracellular ligand may comprise CDR3 from the heavy chain variable region of ofatumumab shown as SEQ ID No. 23 and/or CDR3 from the light chain variable region of ofatumumab shown as SEQ ID No. 24. The extracellular ligand may comprise CDR1, CDR2 and CDR3 from the heavy chain variable region of ofatumumab shown as SEQ ID No. 23 and/or CDR1, CDR2 and CDR3 from the light chain variable region of ofatumumab shown as SEQ ID No. 24.

Rituximab and Ofatumumab (and possibly Veltuzumab) are ideal for the FAS trigger for the suicide gene of the present invention since they cause clustering of CD20 and are intrinsically highly lytic and especially Rituximab has a very well established safety profile. On occasion, a Rituxumab triggered suicide gene may be impractical—this would be in patients who regularly receive Rituximab, particularly maintenance rituximab. Since Rituximab has such a long half-life and the suicide gene-approach we are developing is likely to have such sensitivity, it may take months after a Rituximab dose to be able to give engineered T-cells. In these patients, having a CD20 variant which was insensitive to Rituximab but sensitive to Ofatumumab would be useful.

Nucleic Acid Sequences

The second aspect of the invention provides a nucleic acid sequence which encodes a chimeric protein according to the invention.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the second aspect of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The nucleic acid sequence may encode the chimeric protein sequence shown as SEQ ID No. 1, SEQ ID No. 2 or a variant thereof.

For example the nucleotide sequence may comprise the sequence shown as SEQ ID No. 25 or 26.

dCD20-FAS

SEQ ID No. 25

ATGGGCCAGAGCTTCTTCATGCGGGAGAGCAAGACCCTGGGAGCCGTGCA

GATCATGAACGGCCTGTTCCACATCGCCCTGGGAGGCCTGCTGATGATCC

CTGCCGGCATCTACGCCCCAATCTGCGTGACCGTGTGGTACCCACTGTGG

GGAGGCATCATGTACATCATCAGCGGCAGCCTGCTGGCCGCCACCGAGAA

GAACAGCCGGAAGTGCCTGGTGAAGGGCAAGATGATCATGAACAGCCTGA

GCCTGTTCGCCGCCATCAGCGGCATGATCCTGAGCATCATGGACATCCTG

AACATCAAGATCAGCCACTTCCTGAAGATGGAGAGCCTGAACTTCATCCG

GGCCCACACCCCATACATCAACATCTACAACTGCGAGCCTGCCAACCCCA

GCGAGAAGAACAGCCCCAGCACCCAGTACTGCTACAGCATCCAGAGCCTG

TTCCTGGGCATCCTGAGCGTGATGCTGATCTTCGCCTTCTTCCAGGAGCT

GGTGATCGCCGGCATCGTGGAGAACGAGTGGAAGCGGACCTGCAGCCGGC

CCAAGAGCAACATCGTGCTGCTGAGCGCCGAAGAGAAGAAAGAGCAGACC

ATCGAGATCAAGGAGGAAGTGGTGGGCCTGACCGAGACCAGCAGCCAGCC

CAAGAACGAGGAGGACATCGAGATCATCCCCATCCAGGAAGAAGAGGAAG

AGGAGACCGAGACCAACTTCCCCGAGCCACCCCAGGACCAGGAGAGCAGC

CCTATCGAGAACGACAGCAGCCCCAGCGGTGGCGGTGGCAGCGAGGTACA

GAAAACATGCAGAAAGCACAGAAAGGAAAACCAAGGTTCTCATGAATCTC

CAACCTTAAATCCTGAAACAGTGGCAATAAATTTATCTGATGTTGACTTG

AGTAAATATATCACCACTATTGCTGGAGTCATGACACTAAGTCAAGTTAA

AGGCTTTGTTCGAAAGAATGGTGTCAATGAAGCCAAAATAGATGAGATCA

AGAATGACAATGTCCAAGACACAGCAGAACAGAAAGTTCAACTGCTTCGT

AATTGGCATCAACTTCATGGAAAGAAAGAAGCGTATGACACATTGATTAA

AGATCTCAAAAAAGCCAATCTTTGTACTCTTGCAGAGAAAATTCAGACTA

TCATCCTCAAGGACATTACTAGTGACTCAGAAAATTCAAACTTCAGAAAT

GAAATCCAAAGCTTGGTCTGA dCD20$_{P172W}$-FAS

SEQ ID No. 26

ATGGGCCAGAGCTTCTTCATGCGGGAGAGCAAGACCCTGGGAGCCGTGCA

GATCATGAACGGCCTGTTCCACATCGCCCTGGGAGGCCTGCTGATGATCC

CTGCCGGCATCTACGCCCCAATCTGCGTGACCGTGTGGTACCCACTGTGG

GGAGGCATCATGTACATCATCAGCGGCAGCCTGCTGGCCGCCACCGAGAA

GAACAGCCGGAAGTGCCTGGTGAAGGGCAAGATGATCATGAACAGCCTGA

GCCTGTTCGCCGCCATCAGCGGCATGATCCTGAGCATCATGGACATCCTG

AACATCAAGATCAGCCACTTCCTGAAGATGGAGAGCCTGAACTTCATCCG

GGCCCACACCCCATACATCAACATCTACAACTGCGAGCCTGCCAACTGGA

GCGAGAAGAACAGCCCCAGCACCCAGTACTGCTACAGCATCCAGAGCCTG

TTCCTGGGCATCCTGAGCGTGATGCTGATCTTCGCCTTCTTCCAGGAGCT

GGTGATCGCCGGCATCGTGGAGAACGAGTGGAAGCGGACCTGCAGCCGGC

CCAAGAGCAACATCGTGCTGCTGAGCGCCGAAGAGAAGAAAGAGCAGACC

ATCGAGATCAAGGAGGAAGTGGTGGGCCTGACCGAGACCAGCAGCCAGCC

CAAGAACGAGGAGGACATCGAGATCATCCCCATCCAGGAAGAAGAGGAAG

AGGAGACCGAGACCAACTTCCCCGAGCCACCCCAGGACCAGGAGAGCAGC

CCTATCGAGAACGACAGCAGCCCCAGCGGTGGCGGTGGCAGCGAGGTACA

GAAAACATGCAGAAAGCACAGAAAGGAAAACCAAGGTTCTCATGAATCTC

CAACCTTAAATCCTGAAACAGTGGCAATAAATTTATCTGATGTTGACTTG

AGTAAATATATCACCACTATTGCTGGAGTCATGACACTAAGTCAAGTTAA

AGGCTTTGTTCGAAAGAATGGTGTCAATGAAGCCAAAATAGATGAGATCA

AGAATGACAATGTCCAAGACACAGCAGAACAGAAAGTTCAACTGCTTCGT

AATTGGCATCAACTTCATGGAAAGAAAGAAGCGTATGACACATTGATTAA

AGATCTCAAAAAAGCCAATCTTTGTACTCTTGCAGAGAAAATTCAGACTA

TCATCCTCAAGGACATTACTAGTGACTCAGAAAATTCAAACTTCAGAAAT

GAAATCCAAAGCTTGGTCTGA

Nucleic Acid Construct

The invention also provides a nucleic acid construct which comprises:

i) a first nucleic acid sequence encoding a chimeric protein which comprises a multi-spanning transmembrane protein fused to a FAS endodomain; and ii) a second nucleic acid sequence encoding a nucleotide of Interest (NOI).

The NOI may, for example encode a T-cell receptor (TCR) or chimeric antigen receptor (CAR).

The nucleic acid sequences may be joined by a sequence allowing co-expression of the two or more nucleic acid sequences. For example, the construct may comprise an internal promoter, an internal ribosome entry sequence (IRES) sequence or a sequence encoding a cleavage site. The cleavage site may be self-cleaving, such that when the polypeptide is produced, it is immediately cleaved into the discrete proteins without the need for any external cleavage activity.

Various self-cleaving sites are known, including the Foot-and-Mouth disease virus (FMDV) 2a self-cleaving peptide, which has the sequence shown as SEQ ID No. 27 or 28:

```
                                           SEQ ID No. 27
RAEGRGSLLTCGDVEENPGP
or
                                           SEQ ID No 28
QCTNYALLKLAGDVESNPGP
```

The co-expressing sequence may be an internal ribosome entry sequence (IRES). The co-expressing sequence may be an internal promoter.

T-Cell Receptor (TCR)

The T cell receptor or TCR is a molecule found on the surface of T cells that is responsible for recognizing antigens bound to major histocompatibility complex (MHC) molecules. The binding between TCR and antigen is of relatively low affinity and is degenerate: many TCR recognize the same antigen and many antigens are recognized by the same TCR.

The TCR is composed of two different protein chains, i.e. it is a heterodimer. In 95% of T cells, this consists of an alpha ($\alpha$) and beta ($\beta$) chain, whereas in 5% of T cells this consists of gamma and delta ($\gamma/\delta$) chains. This ratio changes during ontogeny and in diseased states.

When the TCR engages with antigenic peptide and MHC (peptide/MHC), the T lymphocyte is activated through a series of biochemical events mediated by associated enzymes, co-receptors, specialized adaptor molecules, and activated or released transcription factors.

The nucleic acid construct or vector of the present invention may comprise a nucleic acid sequence encoding a TCR $\alpha$ chain, a TCR $\beta$ chain, a TCR$\gamma$ chain or a TCR $\delta$ chain. It may, for example, comprise a nucleic acid sequence encoding a TCR $\alpha$ chain and a nucleic acid sequence encoding a TCR $\beta$ chain; or a nucleic acid sequence encoding a TCR$\gamma$ chain or a nucleic acid sequence encoding a TCR $\delta$ chain. The two nucleic acid sequences may be joined by a sequence enabling co-expression of the two TCR chains, such as an internal promoter, an IRES sequence or a cleavage site such as a self-cleaving site.

Chimeric Antigen Receptors (CARs)

The nucleic acid sequence of interest (NOI) may encode a chimeric antigen receptor (CAR).

Classical CARs are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antigen binding site such as a ligand. A spacer domain may be necessary to isolate the binder from the membrane and to allow it a suitable orientation. A common spacer domain used is the Fc of IgG1. More compact spacers can suffice e.g. the stalk from CD8$\alpha$ and even just the IgG1 hinge alone, depending on the antigen. A trans-membrane domain anchors the protein in the cell membrane and connects the spacer to the endodomain which may comprise or associate with an intracellular signalling domain.

Early CAR designs had intracellular signalling domains derived from the intracellular parts of either the $\zeta$ chain of the Fc$\epsilon$R1 or CD3$\zeta$. Consequently, these first generation receptors transmitted immunological signal 1, which was sufficient to trigger T-cell killing of cognate target cells but failed to fully activate the T-cell to proliferate and survive.

To overcome this limitation, compound signalling domains have been constructed: fusion of the intracellular part of a T-cell co-stimulatory molecule to that of CD3$\zeta$ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have intracellular signalling domains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

Vector

In a third aspect, the present invention provides a vector which comprises a nucleic acid sequence or nucleic acid construct of the invention.

The present invention also provides a vector, or kit of vectors which comprises one or more nucleic acid sequence(s) or nucleic acid construct(s) of the invention and optionally one of more additions nucleic acid sequences of interest (NOI). Such a vector may be used to introduce the nucleic acid sequence(s) or nucleic acid construct(s) into a host cell so that it expresses one or more chimeric protein(s) according to the first aspect of the invention and optionally one or more other proteins of interest (POI). The kit may also comprise an extracellular ligand.

The vector may, for example, be a plasmid or a viral vector, such as a retroviral vector or a lentiviral vector, or a transposon based vector or synthetic mRNA.

The vector may be capable of transfecting or transducing a T cell.

The NOI may, for example encode a chimeric antigen receptor or a T-cell receptor, such that when the vector is used to transduce a target cell, the target cell co-expresses a chimeric protein and a chimeric antigen receptor or T-cell receptor.

Cell

The present invention also relates to a cell comprising a chimeric protein according to the first aspect of the invention.

The cell may, for example, be an immune cell such as a T-cell or a natural killer (NK) cell.

The cell may be a stem cell such as a haematopoietic stem cell.

T cells or T lymphocytes which are a type of lymphocyte that plays a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+ FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

Natural Killer Cells (or NK cells) are a type of cytolytic cell which form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

Stem cells are undifferentiated cells which can differentiate into specialized cells. In mammals, there are two broad types of stem cells: embryonic stem cells, which are isolated from the inner cell mass of blastocysts, and adult stem cells, which are found in various tissues. In adult organisms, stem cells and progenitor cells act as a repair system for the body, replenishing adult tissues. In a developing embryo, stem cells can differentiate into all the specialized cells—ectoderm, endoderm and mesoderm (see induced pluripotent stem cells)—but also maintain the normal turnover of regenerative organs, such as blood, skin, or intestinal tissues.

There are three known accessible sources of autologous adult stem cells in humans:
1. Bone marrow, which requires extraction by harvesting, i.e. drilling into bone.
2. Adipose tissue, which requires extraction by liposuction.
3. Blood, which requires extraction through apheresis, wherein blood is drawn from the donor and passed through a machine that extracts the stem cells and returns other portions of the blood to the donor.

Adult stem cells are frequently used in medical therapies, for example in bone marrow transplantation. Stem cells can now be artificially grown and transformed (differentiated) into specialized cell types with characteristics consistent with cells of various tissues such as muscles or nerves. Embryonic cell lines and autologous embryonic stem cells generated through Somatic-cell nuclear transfer or dedifferentiation can also be used to generate specialised cell types for cell therapy.

Hematopoietic stem cells (HSCs) are the blood cells that give rise to all the other blood cells and are derived from mesoderm. They are located in the red bone marrow, which is contained in the core of most bones.

They give rise to the myeloid (monocytes and macrophages, neutrophils, basophils, eosinophils, erythrocytes, megakaryocytes/platelets, dendritic cells), and lymphoid lineages (T-cells, B-cells, NK-cells). The hematopoietic tissue contains cells with long-term and short-term regeneration capacities and committed multipotent, oligopotent, and unipotent progenitors.

HSCs are a heterogeneous population. Three classes of stem cells exist, distinguished by their ratio of lymphoid to myeloid progeny (L/M) in blood. Myeloid-biased (My-bi) HSC have low L/M ratio (between 0 and 3), whereas lymphoid-biased (Ly-bi) HSC show a large ratio (>10). The third category consists of the balanced (Bala) HSC, whose L/M ratio is between 3 and 10. Only the myeloid-biased and balanced HSCs have durable self-renewal properties.

The chimeric protein-expressing cells of the invention may be any of the cell types mentioned above.

T or NK cells expressing one or more chimeric protein(s) according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells expressing one or more chimeric protein(s) according to the first aspect of the invention may be derived from ex vivo differentiation of inducible progenitor cells or embryonic progenitor cells to T cells. Alternatively, an immortalized T-cell line which retains its lytic function and could act as a therapeutic may be used.

In all these embodiments, chimeric protein(s)-expressing cells are generated by introducing DNA or RNA coding for the, or each, chimeric protein, and optionally an NOI by means such as transduction with a viral vector or transfection with DNA or RNA.

The cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding one or more chimeric protein(s) according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) according to the second aspect of the invention.

The present invention also provides a kit which comprises a T or NK cell comprising one or more chimeric protein(s) according to the first aspect of the invention and a CID.

Pharmaceutical Composition

The present invention also relates to a pharmaceutical composition containing a plurality of cells according to the fourth aspect of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Methods

The invention also provides a method for making a cell according to the fourth aspect of the invention which comprises the step of transducing or transfecting a cell with a vector according to the third aspect of the invention.

The vector may, for example, be a retroviral or lentiviral vector.

The invention also provides a method for deleting a cell according to the fourth aspect of the invention, which comprises the step of exposing the cells to an extracellular ligand which binds to the multi-spanning transmembrane protein.

Binding of the extracellular ligand may leads to activation of the FAS endodomain and apoptosis of the cell.

Binding of the extracellular ligand may lead to cross-linking of multi-spanning transmembrane proteins of a plurality of chimeric proteins, leading to complement dependent cytotoxicity (CDC).

Where the extracellular ligand is an antibody, binding of the extracellular ligand may lead to antibody-dependent cell-mediated cytotoxicity (ADCC).

The cells may be exposed to the extracellular ligand in vivo or in vitro.

The extracellular ligand may be, for example, an antiCD20 mAb such as Rituximab, Ofatumumab or Veltuzumab.

The extracellular ligand may be administered in the form of a pharmaceutical composition. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

The invention also provides a method for preventing and/or treating a pathological immune reaction in a subject caused by administration of a cell according to the fourth aspect of the invention to the subject, which comprises the step of administering an extracellular ligand, capable of binding the multi-spanning transmembrane protein, to the subject.

The pathological immune reaction may be selected from the following group: graft-versus-host disease; on-target, off-tumour toxicity; immune activation syndrome; and lymphoproliferative disorders.

The invention also provides a method for treating or preventing a disease in a subject, which comprises the step of administering a cell according to the fourth aspect of the invention to the subject. The cell may be in the form of a pharmaceutical composition as defined above.

The method may comprises the following steps:
(i) transducing or transfecting a sample of cells isolated from a subject with a vector according to the third aspect of the invention, and
(ii) administering the transduced/transfected cells to a patient.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the immune cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The methods for treating a disease provided by the present invention may involve monitoring the progression of the disease and monitoring any toxic activity and adjusting the dose of the extracellular ligand administered to the subject to provide acceptable levels of disease progression and toxic activity.

Monitoring the progression of the disease means to assess the symptoms associated with the disease over time to determine if they are reducing/improving or increasing/worsening.

Toxic activities relate to adverse effects caused by the cells of the invention following their administration to a subject. Toxic activities may include, for example, immunological toxicity, biliary toxicity and respiratory distress syndrome.

In particular the invention provides a method for treating a disease in a subject, which comprises the following steps:
(i) administering a cell according to the fourth aspect of the invention to the subject;
(ii) monitoring the subject for the development of a pathological immune reaction; and
(iii) administering rapamycin or a rapamycin analogue to the subject if the subject shows signs of developing or having developed a pathological immune reaction.

The present invention provides a cell of the present invention for use in treating and/or preventing a disease.

The cell may, for example, be for use in haematopoietic stem cell transplantation, lymphocyte infusion or adoptive cell transfer.

The invention also relates to the use of a cell of the present invention in the manufacture of a medicament for the treatment and/or prevention of a disease.

The present invention also provides an extracellular ligand capable of activating a chimeric protein according to the first aspect of the invention for use in treating and/or preventing a toxic activity.

The disease to be treated and/or prevented by the cells and methods of the present invention may be an infection, such as a viral infection.

The methods of the invention may also be for the control of pathogenic immune responses, for example in autoimmune diseases, allergies and graft-vs-host rejection.

Where the cells of the invention express a TCR or CAR, they may be useful for the treatment of a cancerous disease, such as bladder cancer, breast cancer, colon cancer, endometrial cancer, kidney cancer (renal cell), leukemia, lung cancer, melanoma, non-Hodgkin lymphoma, pancreatic cancer, prostate cancer and thyroid cancer.

The TCR/CAR-expressing cells of the present invention may be capable of killing target cells, such as cancer cells.

The cells of the present invention may be used in any cellular therapy in which modified or unmodified cells are administered to a patient. An example of a cellular therapy is adoptive T cell transfer after CD34+ stem cell transplantation. Administering T cells after stem cell transfer helps to accelerate the reconstitution of an immune system in the patient recipient. When a matched related or unrelated donor is not available, or the disease is too aggressive for an extensive donor search, the use of an HLA haploidentical family donor may be effective. Such donors may be parents, siblings, or second-degree relatives. Such infusions may enhance immune recovery and thereby reduce virus infections and eliminate relapsing leukemia cells. However, the coexistence of alloreactive T cells in a donor stem cell graft may cause graft-versus-host disease (GvHD) in which the donor cells react against the recipient, which may progressively damage the skin, gut, liver, and other organs of the recipient.

Other examples of cell therapies include using native cells or cells genetically engineered to express a heterologous gene. These treatments are used for many disorders, including blood disorders, but these therapies may have negative side effects. In another method, immature progenitor cells that can differentiate into many types of mature cells, such as, for example, mesenchymal stromal cells, may be used to treat disorders by replacing the function of diseased cells. There present invention provides a rapid and effective mechanism to remove possible negative effects of donor cells used in cellular therapy.

The present invention provides a method of reducing the effect of graft versus host disease in a human patient following donor T cell transplantation, comprising transfecting or transducing human donor T cells in a donor cell culture with vector according to the present invention; administering the transduced or transfected donor T cells to the patient; subsequently detecting the presence or absence of graft versus host disease in the patient; and administering an extracellular ligand to a patient for whom the presence of graft versus host disease is detected. The T cells may be non-allodepleted.

The present invention provides a method of stem cell transplantation, comprising administering a haploidentical stem cell transplant to a human patient; and administering haploidentical donor T cells to the patient, wherein the T cells are transfected or transduced in a haploidentical donor cell culture with a vector according to the invention.

The cells may be non-allodepleted human donor T cells in a donor cell culture.

The present invention also provides a method of stem cell transplantation, comprising administering a haploidentical stem cell transplant to a human patient; and administering non-allodepleted haploidentical donor T cells to the patient, wherein the T cells are transfected or transduced in a haploidentical donor cell culture with vector according to the invention.

The haploidentical stem cell transplant may be a CD34+ haploididentical stem cell transplant. The human donor T cells may be haploidentical to the patient's T cells. The patient may any disease or disorder which may be alleviated by stem cell transplantation. The patient may have cancer, such as a solid tumour or cancer of the blood or bone marrow. The patient may have a blood or bone marrow disease. The patient may have sickle cell anemia or metachromatic leukodystrophy.

The donor cell culture may be prepared from a bone marrow sample or from peripheral blood. The donor cell culture may be prepared from donor peripheral blood mononuclear cells. In some embodiments, the donor T cells are allodepleted from the donor cell culture before transfection or transduction. Transduced or transfected T cells may be cultured in the presence of IL-2 before administration to the patient.

The invention will now be further described by way of Examples, which are meant to serve to assist one of ordinary skill in the art in carrying out the invention and are not intended in any way to limit the scope of the invention.

EXAMPLES

Example 1—Testing Truncated Versions of CD20

CD20 is a multi-spanning membrane protein expressed on B cells and on almost all B-cell lymphomas, hairy cell leukemia and B-cell chronic lymphocytic leukemia. CD20 has two extracellular loops: a minor loop and a major loop constrained by a di-sulfide bond. It has an amino-terminal and carboxy-terminal endodomain.

CD20 is recognised by a number of therapeutic monoclonal antibodies, including Rituximab and Ofatumumab. The present inventors sought to determine whether CD20 with a deletion of the amino or carboxy endodomain termini could still be recognised by such antibodies.

Figure 1:
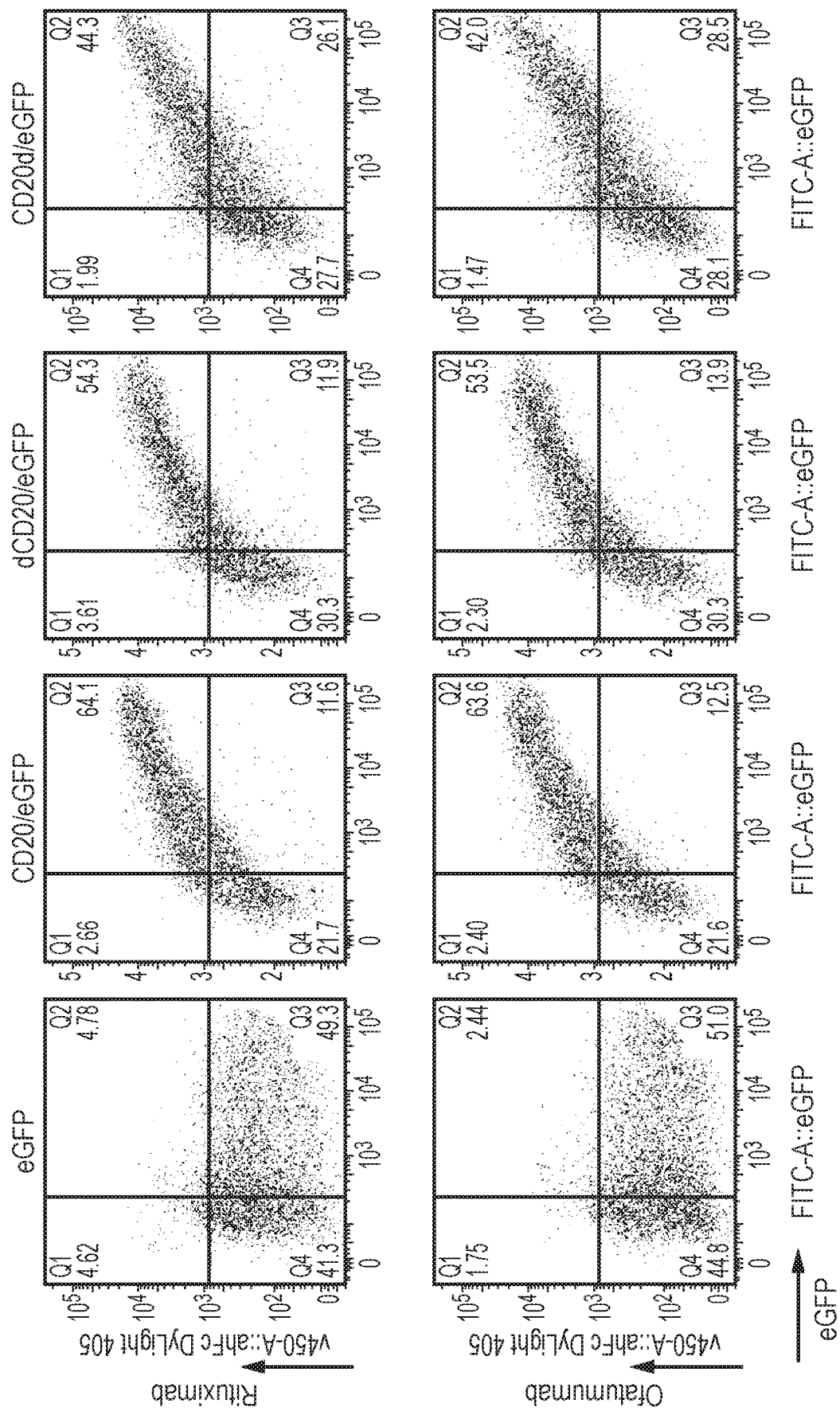
FIG. 1: Recognition of truncations of CD20 by Rituximab and Ofatumumab

To this end: full-length CD20; an amino-terminal (endodomain) truncate of CD20; and a carboxy-terminal (endodomain) truncate of CD20 were each fused with eGFP. 293T cells were transfected with these plasmids and stained with Rituxumab or Ofatumumab. Flow-cytometric analysis showed that these truncations made no difference to surface expression/recognition of CD20 (FIG. 1).

Example 2—Production of a FAS Chimera with Low Basal Toxicity

Expression of a simple FAS chimera (for example a fusion between RQR8 and FAS), or a chimeric antigen receptor with a FAS endodomain (Tone et al (2013) Hum. Gene Ther. Methods 24, 141-150) results in significant basal toxicity. Since FAS is such a sensitive trigger of apoptosis, it may be that simple over-expression leads to spontaneous activation.

In order to test this, a FAS chimera was generated which was a fusion between a multi-membrane spanning protein and FAS. This should result in "padding out" the FAS endodomains, reducing the probability of spontaneous activation and hence reducing or eliminating basal toxicity. CD20 was chosen as the multi-spanning protein and the carboxy-terminus of the amino-terminally truncated version of CD20 was fused to the endodomain of FAS, to create dCD20-FAS (FIG. 2b).

The constructs also co-expressed eGFP which enables their expression and function to be studied. RQR8 and RQR8-FAS, a variant of RQR8 where FAS is attached to the carboxy-terminus of RQR8, were also included. Function was tested in 293T cells, comparing their basal toxicity and toxicity induced by exposure to Ofatumumab. The results are shown in FIG. 3. Unlike RQR8-FAS which had high levels of basal toxicity, dCD20-FAS resulted in very low basal toxicity and very high induced toxicity.

Example 3—Investigating Sensitivity to Rituximab

Jurkat T-cells were transduced with dCD20-FAS and exposed to different concentrations of Rituximab (without complement) and a time-course performed. FAS mediated apoptosis is expected to activate relatively slowly. Apoptosis was determined by staining T-cells with Annexin-V/7AAD. Remarkably, as shown in FIG. 4, in the 24 and 48 h time course the concentration of Rituximab which kills 50% of cells is below 3.125 ug/ml. Further experiments were performed where killing of dCD20-FAS expressing T-cells were exposed to further dilutions of Rituximab for 48 hours (FIG. 5). This experiment indicated that dCD20-FAS affords a very sensitive activation with percentage which kills 50% of cells being approximately 0.6 ug/ml. this is well below the ~200 ug/ml therapeutic levels (Berinstein et al. (1998) Ann. Oncol. Off. J. Eur. Soc. Med. Oncol. ESMO 9, 995-1001).

Example 4—Investigating Sensitivity to Ofatumumab

Jurkat T-cells were transduced with dCD20-FAS and exposed to different concentrations of Ofatumumab and a time course performed (FIG. 6). T-cells are remarkably sensitive to Ofatumumab. Killing occurred faster and at lower concentrations than with Rituximab. In order to determine the sensitivity of dCD20-FAS expressing T-cells, further experiments were performed where killing of dCD20-FAS T-cells after 48 hours exposure to increasing dilutions of Ofatumumab was determined (FIG. 7). Remarkably, the concentration of Ofatumumab where 50% of the T-cells were killed was not reached, with this concentration being below 0.195 ug/ml. This is well below the therapeutic concentrations of Ofatumumab which are reported to be between 63 ug/ml and 1482 ug/ml (after the first infusion of Ofatumumab and $12^{th}$ respectively) (Gravanis et al. (2010) The Oncologist; 15:1335-1343).

Example 5—Engineering CD20 to Disrupt Rituximab, but not Ofatumumab Binding

There may be situations in which Rituximab is not an ideal activating drug, for instance in patient groups who regularly receive Rituximab. In these patients, insensitivity to Rituximab but sensitivity to Ofatumumab would be a useful approach since Ofatumumab is uncommonly used but appears to be equally or more effective than Rituximab.

In order to produce a CD20 variant, a number of mutations were introduced to CD20 at residue A170 and P172 which were predicted to displace Rituximab binding but not effect Ofatumumab binding. From these mutations it was found that P172W mutated CD20 binds Ofatumumab, but not Rituxumab. This is confirmed by the results shown in FIG. 8 where wt CD20 and CD20-P172W were co-expressed with eGFP and transfected into 293T cells. These cells were subsequently stained with either Rituximab or Ofatumumab. While the wt CD20 binds both, the CD20-P172W only binds Ofatumumab.

Example 6—Studying ADCC

Since ADCC occurs within the time-frame of direct killing, a mutant of dCD20-FAS was generated where the FAS endodomain was inactivated using a point mutation (E272K) (Wang et al., (2010), Nature Structural and Molecular Biology, 17, 11, 1324-1330). T-cells are transduced with this construct. Natural killer (NK) cell effectors are generated using a K562 stimulator cell line, expressing membrane-bound interleukin-15 and 41BBL established by retroviral vector transduction and single-cell cloning (K562.41BBL.mIL150. Freshly isolated peripheral blood mononuclear cells from healthy donors are co-cultured 1:1 in 24-well tissue-culture-treated multi-well plates with irradiated K562.41BBL.mIL15, irradiated at 120 Gy and supplemented with 40 iu IL2. Partial media changes are performed as required. Following 7 days in culture, a pure population (~95% purity) of NK cells is isolated following a single round of Miltenyi CD56-positive selection and labelled with CellTRACE violet (invitrogen). T-cells transduced with either full-length CD20, RQR8 or dCD20-$FAS_{E272K}$ are used as targets and are co-cultured with NK cell effectors at effector:target ratios of 16:1, 8:1, 4:1, and 2:1 for 48 hours. Cellular deletion is assessed by flow cytometry following Annexin V (BD Biosciences) and propidium iodide (PI) (SigmaAldrich) staining.

Example 7—Studying the Function of dCD20-FAS and dCD20$_{P172W}$-FAS in Primary Human T-Cells The ability of the constructs dCD20-FAS and dCD20P172W-FAS to directly activate apoptosis upon exposure to Rituxumab and Ofatumumab was investigated in primary human T-cells. Since FAS activation takes some time to develop and CDC is almost instantaneous, by testing immediate apoptosis in the presence of complement, it was possible to determine whether these constructs also allow CDC mediated killing. As shown in FIG. 9, dCD20-FAS T-cells were effectively directly killed and killed by CDC by both Rituximab and Ofatumuamb. dCD20$_{P172W}$-FAS primary T-cells, on the other hand, were effectively directly killed or killed by CDC only with Ofatumumab and not with Rituximab. An example of direct killing with dCD20-FAS in primary T-cells by Ofatumuamb is shown in FIG. 10.

The present inventors have therefore generated a triple-function suicide gene which is activated by therapeutic monoclonal antibodies.

All documents referred to herein are hereby incorporated by reference in their entirety, with special attention to the subject matter for which they are referred. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A chimeric protein comprising a multi-spanning transmembrane protein fused to a FAS endodomain,
wherein the multi-spanning transmembrane protein comprises CD20 truncated at the amino-terminus so that it lacks up to 41 amino acids from the CD20 amino-terminus, or at the carboxy-terminus so that it lacks up to 61 amino acids from the CD20 carboxy-terminus, and
wherein the multi-spanning transmembrane protein binds at least one extracellular ligand selected from Rituxumab, Ofatumumab or Veltuzumab, leading to activation of the FAS endodomain.

2. The chimeric protein according to claim 1, which comprises a FAS endodomain fused to the carboxy-terminus of a truncated version of CD20, lacking up to 41 amino acids from the CD20 amino-terminus.

3. The chimeric protein according to claim 1, wherein the FAS endodomain comprises the sequence shown in SEQ ID NO: 20.

4. The chimeric protein according to claim 1, wherein the FAS endodomain comprises the amino acid sequence of SEQ ID NO: 29.

5. A chimeric protein comprising a multi-spanning transmembrane protein that consists of the amino acid sequence of SEQ ID NO: 4, SEQ ID NO: 5, or SEQ ID NO: 6 fused to a FAS endodomain, wherein the multi-spanning transmembrane protein binds at least one extracellular ligand selected from Rituxumab, Ofatumumab or Veltuzumab, leading to activation of the FAS endodomain.

6. The chimeric protein according to claim 5, wherein the FAS endodomain comprises the sequence shown in SEQ ID NO: 20.

7. The chimeric protein according to claim 5, wherein the FAS endodomain comprises the amino acid sequence of SEQ ID NO: 29.

8. A chimeric protein comprising:
a multi-spanning transmembrane protein fused to a FAS endodomain,
wherein the multi-spanning transmembrane protein comprises the amino acid sequence of SEQ ID NO: 3 truncated at the amino terminus so that it lacks up to 41 amino acids from the amino-terminus of SEQ ID NO: 3, or truncated at the carboxy-terminus so that it lacks up to 61 amino acids from the carboxy-terminus of SEQ ID NO: 3, and optionally has one or both of the following substitution mutations:
(a) an amino acid substitution at position A170 of SEQ ID NO: 3;
(b) an amino acid substitution at position P172 of SEQ ID NO: 3; and
wherein the multi-spanning transmembrane protein binds at least one extracellular ligand selected from Rituxumab, Ofatumumab or Veltuzumab, leading to activation of the FAS endodomain.

9. The chimeric protein according to claim 8 that comprises the mutation P172W, with position 172 defined with reference to the full length CD20 sequence shown as SEQ ID NO: 3.

10. The chimeric protein according to claim 8, wherein the FAS endodomain comprises the amino acid sequence of SEQ ID NO: 29.

11. The chimeric protein according to claim 8, wherein the FAS endodomain comprises the sequence shown in SEQ ID NO: 20.

12. An isolated cell which expresses the chimeric protein according to claim 1.

13. An isolated cell which expresses the chimeric protein according to claim 5.

14. An isolated cell which expresses the chimeric protein according to claim 6.

15. An isolated cell which expresses the chimeric protein according to claim 3.

16. An isolated cell which expresses the chimeric protein according to claim 4.

17. An isolated cell which expresses the chimeric protein according to claim 7.

18. An isolated cell which expresses the chimeric protein according to claim 8.

19. An isolated cell which expresses the chimeric protein according to claim 9.

20. An isolated cell which expresses the chimeric protein according to claim 10.

21. An isolated cell which expresses the chimeric protein according to claim 11.

* * * * *

SEQUENCE LISTING

<160> NUMBER OF SEQ ID NOS: 29

<210> SEQ ID NO 1
<211> LENGTH: 406
<212> TYPE: PRT

<213> ORGANISM: Artificial Sequence
<220> FEATURE:
<223> OTHER INFORMATION: chimeric protein

<400> SEQUENCE: 1

```
Met Gly Gln Ser Phe Phe Met Arg Glu Ser Lys Thr Leu Gly Ala Val
1               5                   10                  15

Gln Ile Met Asn Gly Leu Phe His Ile Ala Leu Gly Gly Leu Leu Met
            20                  25                  30

Ile Pro Ala Gly Ile Tyr Ala Pro Ile Cys Val Thr Val Trp Tyr Pro
        35                  40                  45

Leu Trp Gly Gly Ile Met Tyr Ile Ile Ser Gly Ser Leu Leu Ala Ala
    50                  55                  60

Thr Glu Lys Asn Ser Arg Lys Cys Leu Val Lys Gly Lys Met Ile Met
65                  70                  75                  80

Asn Ser Leu Ser Leu Phe Ala Ala Ile Ser Gly Met Ile Leu Ser Ile
                85                  90                  95

Met Asp Ile Leu Asn Ile Lys Ile Ser His Phe Leu Lys Met Glu Ser
            100                 105                 110

Leu Asn Phe Ile Arg Ala His Thr Pro Tyr Ile Asn Ile Tyr Asn Cys
        115                 120                 125

Glu Pro Ala Asn Pro Ser Glu Lys Asn Ser Pro Ser Thr Gln Tyr Cys
    130                 135                 140

Tyr Ser Ile Gln Ser Leu Phe Leu Gly Ile Leu Ser Val Met Leu Ile
145                 150                 155                 160

Phe Ala Phe Phe Gln Glu Leu Val Ile Ala Gly Ile Val Glu Asn Glu
                165                 170                 175

Trp Lys Arg Thr Cys Ser Arg Pro Lys Ser Asn Ile Val Leu Leu Ser
            180                 185                 190

Ala Glu Glu Lys Lys Glu Gln Thr Ile Glu Ile Lys Glu Glu Val Val
        195                 200                 205

Gly Leu Thr Glu Thr Ser Ser Gln Pro Lys Asn Glu Glu Asp Ile Glu
    210                 215                 220

Ile Ile Pro Ile Gln Glu Glu Glu Glu Glu Thr Glu Thr Asn Phe
225                 230                 235                 240

Pro Glu Pro Pro Gln Asp Gln Glu Ser Ser Pro Ile Glu Asn Asp Ser
                245                 250                 255

Ser Pro Ser Gly Gly Gly Ser Glu Val Gln Lys Thr Cys Arg Lys
            260                 265                 270

His Arg Lys Glu Asn Gln Gly Ser His Glu Ser Pro Thr Leu Asn Pro
        275                 280                 285

Glu Thr Val Ala Ile Asn Leu Ser Asp Val Asp Leu Ser Lys Tyr Ile
    290                 295                 300

Thr Thr Ile Ala Gly Val Met Thr Leu Ser Gln Val Lys Gly Phe Val
305                 310                 315                 320

Arg Lys Asn Gly Val Asn Glu Ala Lys Ile Asp Glu Ile Lys Asn Asp
                325                 330                 335

Asn Val Gln Asp Thr Ala Glu Gln Lys Val Gln Leu Leu Arg Asn Trp
            340                 345                 350

His Gln Leu His Gly Lys Lys Glu Ala Tyr Asp Thr Leu Ile Lys Asp
        355                 360                 365

Leu Lys Lys Ala Asn Leu Cys Thr Leu Ala Glu Lys Ile Gln Thr Ile
    370                 375                 380

Ile Leu Lys Asp Ile Thr Ser Asp Ser Glu Asn Ser Asn Phe Arg Asn
```

Glu Ile Gln Ser Leu Val
            405

<210> SEQ ID NO 2
<211> LENGTH: 406
<212> TYPE: PRT
<213> ORGANISM: Artificial Sequence
<220> FEATURE:
<223> OTHER INFORMATION: chimeric protein

<400> SEQUENCE: 2

Met Gly Gln Ser Phe Phe Met Arg Glu Ser Lys Thr Leu Gly Ala Val
1               5                   10                  15

Gln Ile Met Asn Gly Leu Phe His Ile Ala Leu Gly Gly Leu Leu Met
            20                  25                  30

Ile Pro Ala Gly Ile Tyr Ala Pro Ile Cys Val Thr Val Trp Tyr Pro
        35                  40                  45

Leu Trp Gly Gly Ile Met Tyr Ile Ile Ser Gly Ser Leu Leu Ala Ala
    50                  55                  60

Thr Glu Lys Asn Ser Arg Lys Cys Leu Val Lys Gly Lys Met Ile Met
65                  70                  75                  80

Asn Ser Leu Ser Leu Phe Ala Ala Ile Ser Gly Met Ile Leu Ser Ile
                85                  90                  95

Met Asp Ile Leu Asn Ile Lys Ile Ser His Phe Leu Lys Met Glu Ser
            100                 105                 110

Leu Asn Phe Ile Arg Ala His Thr Pro Tyr Ile Asn Ile Tyr Asn Cys
        115                 120                 125

Glu Pro Ala Asn Trp Ser Glu Lys Asn Ser Pro Ser Thr Gln Tyr Cys
    130                 135                 140

Tyr Ser Ile Gln Ser Leu Phe Leu Gly Ile Leu Ser Val Met Leu Ile
145                 150                 155                 160

Phe Ala Phe Phe Gln Glu Leu Val Ile Ala Gly Ile Val Glu Asn Glu
                165                 170                 175

Trp Lys Arg Thr Cys Ser Arg Pro Lys Ser Asn Ile Val Leu Leu Ser
            180                 185                 190

Ala Glu Glu Lys Lys Glu Gln Thr Ile Glu Ile Lys Glu Glu Val Val
        195                 200                 205

Gly Leu Thr Glu Thr Ser Ser Gln Pro Lys Asn Glu Glu Asp Ile Glu
    210                 215                 220

Ile Ile Pro Ile Gln Glu Glu Glu Glu Glu Thr Glu Thr Asn Phe
225                 230                 235                 240

Pro Glu Pro Pro Gln Asp Gln Glu Ser Ser Pro Ile Glu Asn Asp Ser
                245                 250                 255

Ser Pro Ser Gly Gly Gly Gly Ser Glu Val Gln Lys Thr Cys Arg Lys
            260                 265                 270

His Arg Lys Glu Asn Gln Gly Ser His Glu Ser Pro Thr Leu Asn Pro
        275                 280                 285

Glu Thr Val Ala Ile Asn Leu Ser Asp Val Asp Leu Ser Lys Tyr Ile
    290                 295                 300

Thr Thr Ile Ala Gly Val Met Thr Leu Ser Gln Val Lys Gly Phe Val
305                 310                 315                 320

Arg Lys Asn Gly Val Asn Glu Ala Lys Ile Asp Glu Ile Lys Asn Asp
                325                 330                 335

Asn Val Gln Asp Thr Ala Glu Gln Lys Val Gln Leu Leu Arg Asn Trp

His Gln Leu His Gly Lys Lys Glu Ala Tyr Asp Thr Leu Ile Lys Asp
            340                 345                 350

Leu Lys Lys Ala Asn Leu Cys Thr Leu Ala Glu Lys Ile Gln Thr Ile
355                 360                 365

Ile Leu Lys Asp Ile Thr Ser Asp Ser Glu Asn Ser Asn Phe Arg Asn
    370                 375                 380

Glu Ile Gln Ser Leu Val
385                 390                 395                 400

405

<210> SEQ ID NO 3
<211> LENGTH: 297
<212> TYPE: PRT
<213> ORGANISM: Homo sapiens

<400> SEQUENCE: 3

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

```
<210> SEQ ID NO 4
<211> LENGTH: 256
<212> TYPE: PRT
<213> ORGANISM: Artificial Sequence
<220> FEATURE:
<223> OTHER INFORMATION: truncated CD20 (dCD20)

<400> SEQUENCE: 4

Gln Ser Phe Phe Met Arg Glu Ser Lys Thr Leu Gly Ala Val Gln Ile
1               5                   10                  15

Met Asn Gly Leu Phe His Ile Ala Leu Gly Gly Leu Leu Met Ile Pro
            20                  25                  30

Ala Gly Ile Tyr Ala Pro Ile Cys Val Thr Val Trp Tyr Pro Leu Trp
        35                  40                  45

Gly Gly Ile Met Tyr Ile Ile Ser Gly Ser Leu Leu Ala Ala Thr Glu
    50                  55                  60

Lys Asn Ser Arg Lys Cys Leu Val Lys Gly Lys Met Ile Met Asn Ser
65                  70                  75                  80

Leu Ser Leu Phe Ala Ala Ile Ser Gly Met Ile Leu Ser Ile Met Asp
                85                  90                  95

Ile Leu Asn Ile Lys Ile Ser His Phe Leu Lys Met Glu Ser Leu Asn
            100                 105                 110

Phe Ile Arg Ala His Thr Pro Tyr Ile Asn Ile Tyr Asn Cys Glu Pro
        115                 120                 125

Ala Asn Pro Ser Glu Lys Asn Ser Pro Ser Thr Gln Tyr Cys Tyr Ser
    130                 135                 140

Ile Gln Ser Leu Phe Leu Gly Ile Leu Ser Val Met Leu Ile Phe Ala
145                 150                 155                 160

Phe Phe Gln Glu Leu Val Ile Ala Gly Ile Val Glu Asn Glu Trp Lys
                165                 170                 175

Arg Thr Cys Ser Arg Pro Lys Ser Asn Ile Val Leu Leu Ser Ala Glu
            180                 185                 190

Glu Lys Lys Glu Gln Thr Ile Glu Ile Lys Glu Glu Val Val Gly Leu
        195                 200                 205

Thr Glu Thr Ser Ser Gln Pro Lys Asn Glu Glu Asp Ile Glu Ile Ile
    210                 215                 220

Pro Ile Gln Glu Glu Glu Glu Glu Thr Glu Thr Asn Phe Pro Glu
225                 230                 235                 240

Pro Pro Gln Asp Gln Glu Ser Ser Pro Ile Glu Asn Asp Ser Ser Pro
                245                 250                 255

<210> SEQ ID NO 5
<211> LENGTH: 237
<212> TYPE: PRT
<213> ORGANISM: Artificial Sequence
<220> FEATURE:
<223> OTHER INFORMATION: truncated CD20 (CD20d)

<400> SEQUENCE: 5

Met Gly Thr Thr Pro Arg Asn Ser Val Asn Gly Thr Phe Pro Ala Glu
1               5                   10                  15

Pro Met Lys Gly Pro Ile Ala Met Gln Ser Gly Pro Lys Pro Leu Phe
            20                  25                  30

Arg Arg Met Ser Ser Leu Val Gly Pro Thr Gln Ser Phe Phe Met Arg
        35                  40                  45

Glu Ser Lys Thr Leu Gly Ala Val Gln Ile Met Asn Gly Leu Phe His
    50                  55                  60
```

```
Ile Ala Leu Gly Gly Leu Leu Met Ile Pro Ala Gly Ile Tyr Ala Pro
 65                  70                  75                  80

Ile Cys Val Thr Val Trp Tyr Pro Leu Trp Gly Gly Ile Met Tyr Ile
             85                  90                  95

Ile Ser Gly Ser Leu Leu Ala Ala Thr Glu Lys Asn Ser Arg Lys Cys
        100                 105                 110

Leu Val Lys Gly Lys Met Ile Met Asn Ser Leu Ser Leu Phe Ala Ala
            115                 120                 125

Ile Ser Gly Met Ile Leu Ser Ile Met Asp Ile Leu Asn Ile Lys Ile
        130                 135                 140

Ser His Phe Leu Lys Met Glu Ser Leu Asn Phe Ile Arg Ala His Thr
145                 150                 155                 160

Pro Tyr Ile Asn Ile Tyr Asn Cys Glu Pro Ala Asn Pro Ser Glu Lys
                165                 170                 175

Asn Ser Pro Ser Thr Gln Tyr Cys Tyr Ser Ile Gln Ser Leu Phe Leu
            180                 185                 190

Gly Ile Leu Ser Val Met Leu Ile Phe Ala Phe Phe Gln Glu Leu Val
        195                 200                 205

Ile Ala Gly Ile Val Glu Asn Glu Trp Lys Arg Thr Cys Ser Arg Pro
    210                 215                 220

Lys Ser Asn Ile Val Leu Leu Ser Ala Glu Glu Lys Lys
225                 230                 235
```

<210> SEQ ID NO 6
<211> LENGTH: 256
<212> TYPE: PRT
<213> ORGANISM: Artificial Sequence
<220> FEATURE:
<223> OTHER INFORMATION: chimeric protein (dCD20 P172W)

<400> SEQUENCE: 6

```
Gln Ser Phe Phe Met Arg Glu Ser Lys Thr Leu Gly Ala Val Gln Ile
  1               5                  10                  15

Met Asn Gly Leu Phe His Ile Ala Leu Gly Gly Leu Leu Met Ile Pro
             20                  25                  30

Ala Gly Ile Tyr Ala Pro Ile Cys Val Thr Val Trp Tyr Pro Leu Trp
        35                  40                  45

Gly Gly Ile Met Tyr Ile Ile Ser Gly Ser Leu Leu Ala Ala Thr Glu
    50                  55                  60

Lys Asn Ser Arg Lys Cys Leu Val Lys Gly Lys Met Ile Met Asn Ser
 65                  70                  75                  80

Leu Ser Leu Phe Ala Ala Ile Ser Gly Met Ile Leu Ser Ile Met Asp
             85                  90                  95

Ile Leu Asn Ile Lys Ile Ser His Phe Leu Lys Met Glu Ser Leu Asn
            100                 105                 110

Phe Ile Arg Ala His Thr Pro Tyr Ile Asn Ile Tyr Asn Cys Glu Pro
        115                 120                 125

Ala Asn Trp Ser Glu Lys Asn Ser Pro Ser Thr Gln Tyr Cys Tyr Ser
    130                 135                 140

Ile Gln Ser Leu Phe Leu Gly Ile Leu Ser Val Met Leu Ile Phe Ala
145                 150                 155                 160

Phe Phe Gln Glu Leu Val Ile Ala Gly Ile Val Glu Asn Glu Trp Lys
                165                 170                 175

Arg Thr Cys Ser Arg Pro Lys Ser Asn Ile Val Leu Leu Ser Ala Glu
            180                 185                 190
```

```
Glu Lys Lys Glu Gln Thr Ile Glu Ile Lys Glu Glu Val Val Gly Leu
        195                 200                 205

Thr Glu Thr Ser Ser Gln Pro Lys Asn Glu Glu Asp Ile Glu Ile Ile
    210                 215                 220

Pro Ile Gln Glu Glu Glu Glu Glu Glu Thr Glu Thr Asn Phe Pro Glu
225                 230                 235                 240

Pro Pro Gln Asp Gln Glu Ser Ser Pro Ile Glu Asn Asp Ser Ser Pro
                245                 250                 255

<210> SEQ ID NO 7
<211> LENGTH: 17
<212> TYPE: PRT
<213> ORGANISM: Artificial Sequence
<220> FEATURE:
<223> OTHER INFORMATION: Rituximab-binding epitope sequence from CD20

<400> SEQUENCE: 7

Cys Glu Pro Ala Asn Pro Ser Glu Lys Asn Ser Pro Ser Thr Gln Tyr
1               5                   10                  15

Cys

<210> SEQ ID NO 8
<211> LENGTH: 10
<212> TYPE: PRT
<213> ORGANISM: Artificial Sequence
<220> FEATURE:
<223> OTHER INFORMATION: cysteine-constrained 7-mer cyclic peptide R15-C

<400> SEQUENCE: 8

Ala Cys Pro Tyr Ala Asn Pro Ser Leu Cys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: cysteine-constrained 7-mer cyclic peptide R3-C

<400> SEQUENCE: 9

Ala Cys Pro Tyr Ser Asn Pro Ser Leu Cys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: cysteine-constrained 7-mer cyclic peptide R7-C

<400> SEQUENCE: 10

Ala Cys Pro Phe Ala Asn Pro Ser Thr Cys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: cysteine-constrained 7-mer cyclic peptide R8-,
      R12-, R18-C

<400> SEQUENCE: 11

Ala Cys Asn Phe Ser Asn Pro Ser Leu Cys
```

<210> SEQ ID NO 12
<211> LENGTH: 10
<212> TYPE: PRT
<213> ORGANISM: Artificial Sequence
<220> FEATURE:
<223> OTHER INFORMATION: cysteine-constrained 7-mer cyclic peptide R14-C

<400> SEQUENCE: 12

Ala Cys Pro Phe Ser Asn Pro Ser Met Cys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: cysteine-constrained 7-mer cyclic peptide R16-C

<400> SEQUENCE: 13

Ala Cys Ser Trp Ala Asn Pro Ser Gln Cys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: cysteine-constrained 7-mer cyclic peptide R17-C

<400> SEQUENCE: 14

Ala Cys Met Phe Ser Asn Pro Ser Leu Cys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: cysteine-constrained 7-mer cyclic peptide R19-C

<400> SEQUENCE: 15

Ala Cys Pro Phe Ala Asn Pro Ser Met Cys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: cysteine-constrained 7-mer cyclic peptide R2-C

<400> SEQUENCE: 16

Ala Cys Trp Ala Ser Asn Pro Ser Leu Cys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: cysteine-constrained 7-mer cyclic peptide R10-C

<400> SEQUENCE: 17

Ala Cys Glu His Ser Asn Pro Ser Leu Cys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: cysteine-constrained 7-mer cyclic peptide R13-C

<400> SEQUENCE: 18

Ala Cys Trp Ala Ala Asn Pro Ser Met Cys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: mimetope of Rituximab

<400> SEQUENCE: 19

Gln Asp Lys Leu Thr Gln Trp Pro Lys Trp Leu Glu
1               5                   10

<210> SEQ ID NO 20
<211> LENGTH: 142
<212> TYPE: PRT
<213> ORGANISM: Artificial Sequence
<220> FEATURE:
<223> OTHER INFORMATION: cytoplasmic domain of FAS

<400> SEQUENCE: 20

Glu Val Gln Lys Thr Cys Arg Lys His Arg Lys Glu Asn Gln Gly Ser
1               5                   10                  15

His Glu Ser Pro Thr Leu Asn Pro Glu Thr Val Ala Ile Asn Leu Ser
            20                  25                  30

Asp Val Asp Leu Ser Lys Tyr Ile Thr Thr Ile Ala Gly Val Met Thr
        35                  40                  45

Leu Ser Gln Val Lys Gly Phe Val Arg Lys Asn Gly Val Asn Glu Ala
    50                  55                  60

Lys Ile Asp Glu Ile Lys Asn Asp Asn Val Gln Asp Thr Ala Glu Gln
65                  70                  75                  80

Lys Val Gln Leu Leu Arg Asn Trp His Gln Leu His Gly Lys Lys Glu
                85                  90                  95

Ala Tyr Asp Thr Leu Ile Lys Asp Leu Lys Lys Ala Asn Leu Cys Thr
            100                 105                 110

Leu Ala Glu Lys Ile Gln Thr Ile Ile Leu Lys Asp Ile Thr Ser Asp
        115                 120                 125

Ser Glu Asn Ser Asn Phe Arg Asn Glu Ile Gln Ser Leu Val
    130                 135                 140

<210> SEQ ID NO 21
<211> LENGTH: 120
<212> TYPE: PRT
<213> ORGANISM: Artificial Sequence
<220> FEATURE:
<223> OTHER INFORMATION: Rituximab heavy chain variable chain sequence

<400> SEQUENCE: 21

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
             35                  40                  45

Gly Ala Ile Tyr Pro Gly Asn Gly Asp Thr Ser Tyr Asn Gln Lys Phe
         50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser
            115                 120

<210> SEQ ID NO 22
<211> LENGTH: 107
<212> TYPE: PRT
<213> ORGANISM: Artificial Sequence
<220> FEATURE:
<223> OTHER INFORMATION: Rituximab light chain variable chain sequence

<400> SEQUENCE: 22

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
             20                  25                  30

His Trp Phe Gln Gln Lys Pro Gly Ser Ser Pro Lys Pro Trp Ile Tyr
         35                  40                  45

Ala Thr Ser Asn Leu Ala Ser Gly Val Pro Val Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg
                100                 105

<210> SEQ ID NO 23
<211> LENGTH: 122
<212> TYPE: PRT
<213> ORGANISM: Artificial Sequence
<220> FEATURE:
<223> OTHER INFORMATION: Ofatumumab heavy chain variable chain sequence

<400> SEQUENCE: 23

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asn Asp Tyr
             20                  25                  30

Ala Met His Trp Val Arg Gln Ala Pro Gly Lys Gly Leu Glu Trp Val
         35                  40                  45

Ser Thr Ile Ser Trp Asn Ser Gly Ser Ile Gly Tyr Ala Asp Ser Val
     50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Ile Gln Tyr Gly Asn Tyr Tyr Tyr Gly Met Asp Val Trp 100                 105                 110
Gly Gln Gly Thr Thr Val Thr Val Ser Ser
            115                 120

<210> SEQ ID NO 24
<211> LENGTH: 107
<212> TYPE: PRT
<213> ORGANISM: Artificial Sequence
<220> FEATURE:
<223> OTHER INFORMATION: Ofatumumab light chain variable chain sequence

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 25
<211> LENGTH: 1221
<212> TYPE: DNA
<213> ORGANISM: Artificial Sequence
<220> FEATURE:
<223> OTHER INFORMATION: nucleic acid sequence encoding chimeric protein
      sequence dCD20-FAS

<400> SEQUENCE: 25
atgggccaga gcttcttcat gcgggagagc aagaccctgg agccgtgca gatcatgaac      60 ggcctgttcc acatcgccct gggaggcctg ctgatgatcc tgccggcat ctacgcccca    120 atctgcgtga ccgtgtggta cccactgtgg ggaggcatca tgtacatcat cagcggcagc    180
ctgctggccg ccaccgagaa gaacagccgg aagtgcctgg tgaagggcaa gatgatcatg    240
aacagcctga gcctgttcgc cgccatcagc ggcatgatcc tgagcatcat ggacatcctg    300
aacatcaaga tcagccactt cctgaagatg gagagcctga cttcatccg ggcccacacc    360 ccatacatca acatctacaa ctgcgagcct gccaacccca gcgagaagaa cagccccagc    420
acccagtact gctacagcat ccagagcctg ttcctgggca tcctgagcgt gatgctgatc    480
ttcgccttct tccaggagct ggtgatcgcc ggcatcgtgg agaacgagtg aagcggacc    540 tgcagccggc ccaagagcaa catcgtgctg ctgagcgccg aagagaagaa agagcagacc    600
atcgagatca aggaggaagt ggtgggcctg accgagacca gcagccagcc caagaacgag    660
gaggacatcg agatcatccc catccaggaa gaagaggaag aggagaccga gaccaacttc    720
cccgagccac cccaggacca ggagagcagc cctatcgaga cgacagcag ccccagcggt    780 ggcggtggca gcgaggtaca gaaaacatgc agaaagcaca gaaggaaaa ccaaggttct    840 catgaatctc caaccttaaa tcctgaaaca gtggcaataa atttatctga tgttgacttg    900
agtaaatata tcaccactat tgctggagtc atgacactaa gtcaagttaa aggctttgtt    960

```
cgaaagaatg gtgtcaatga agccaaaata gatgagatca agaatgacaa tgtccaagac    1020
acagcagaac agaaagttca actgcttcgt aattggcatc aacttcatgg aaagaaagaa    1080
gcgtatgaca cattgattaa agatctcaaa aaagccaatc tttgtactct tgcagagaaa    1140
attcagacta tcatcctcaa ggacattact agtgactcag aaaattcaaa cttcagaaat    1200
gaaatccaaa gcttggtctg a                                              1221
```

<210> SEQ ID NO 26
<211> LENGTH: 1221
<212> TYPE: DNA
<213> ORGANISM: Artificial Sequence
<220> FEATURE:
<223> OTHER INFORMATION: nucleic acid sequence encoding chimeric protein sequence (dCD20P172W-FAS)

<400> SEQUENCE: 26

```
atgggccaga gcttcttcat gcgggagagc aagaccctgg agccgtgca gatcatgaac     60 ggcctgttcc acatcgccct gggaggcctg ctgatgatcc ctgccggcat ctacgcccca    120
atctgcgtga ccgtgtggta cccactgtgg ggaggcatca tgtacatcat cagcggcagc    180
ctgctggccg ccaccgagaa gaacagccgg aagtgcctgg tgaagggcaa gatgatcatg    240
aacagcctga gcctgttcgc cgccatcagc ggcatgatcc tgagcatcat ggacatcctg    300
aacatcaaga tcagccactt cctgaagatg gagagcctga acttcatccg ggcccacacc    360
ccatacatca acatctacaa ctgcgagcct gccaactgga gcgagaagaa cagccccagc    420
acccagtact gctacagcat ccagagcctg ttcctgggca tcctgagcgt gatgctgatc    480
ttcgccttct tccaggagct ggtgatcgcc ggcatcgtgg agaacgagtg gaagcggacc    540
tgcagccggc ccaagagcaa catcgtgctg ctgagcgccg aagagaagaa agagcagacc    600
atcgagatca aggaggaagt ggtgggcctg accgagacca gcagccagcc caagaacgag    660
gaggacatcg agatcatccc catccaggaa gaagaggaag aggagaccga gaccaacttc    720
cccgagccac cccaggacca ggagagcagc cctatcgaga cgacagcag ccccagcggt    780 ggcggtggca gcgaggtaca gaaaacatgc agaaagcaca gaaggaaaa ccaaggttct    840 catgaatctc caaccttaaa tcctgaaaca gtggcaataa atttatctga tgttgacttg    900
agtaaatata tcaccactat tgctggagtc atgacactaa gtcaagttaa aggctttgtt    960
cgaaagaatg gtgtcaatga agccaaaata gatgagatca agaatgacaa tgtccaagac    1020
acagcagaac agaaagttca actgcttcgt aattggcatc aacttcatgg aaagaaagaa    1080
gcgtatgaca cattgattaa agatctcaaa aaagccaatc tttgtactct tgcagagaaa    1140
attcagacta tcatcctcaa ggacattact agtgactcag aaaattcaaa cttcagaaat    1200
gaaatccaaa gcttggtctg a                                              1221
```

<210> SEQ ID NO 27
<211> LENGTH: 20
<212> TYPE: PRT
<213> ORGANISM: Foot-and-mouth disease virus

<400> SEQUENCE: 27

```
Arg Ala Glu Gly Arg Gly Ser Leu Leu Thr Cys Gly Asp Val Glu Glu
1               5                   10                  15

Asn Pro Gly Pro
            20
```

<210> SEQ ID NO 28

```
<211> LENGTH: 20
<212> TYPE: PRT
<213> ORGANISM: Foot-and-mouth disease virus

<400> SEQUENCE: 28

Gln Cys Thr Asn Tyr Ala Leu Leu Lys Leu Ala Gly Asp Val Glu Ser
1               5                   10                  15

Asn Pro Gly Pro
            20

<210> SEQ ID NO 29
<211> LENGTH: 85
<212> TYPE: PRT
<213> ORGANISM: Artificial Sequence
<220> FEATURE:
<223> OTHER INFORMATION: "death domain" of FAS

<400> SEQUENCE: 29

Ser Lys Tyr Ile Thr Thr Ile Ala Gly Val Met Thr Leu Ser Gln Val
1               5                   10                  15

Lys Gly Phe Val Arg Lys Asn Gly Val Asn Glu Ala Lys Ile Asp Glu
            20                  25                  30

Ile Lys Asn Asp Asn Val Gln Asp Thr Ala Glu Gln Lys Val Gln Leu
        35                  40                  45

Leu Arg Asn Trp His Gln Leu His Gly Lys Lys Glu Ala Tyr Asp Thr
    50                  55                  60

Leu Ile Lys Asp Leu Lys Lys Ala Asn Leu Cys Thr Leu Ala Glu Lys
65                  70                  75                  80

Ile Gln Thr Ile Ile
                85
```